(12) United States Patent
Muller et al.

(10) Patent No.: US 7,786,080 B2
(45) Date of Patent: Aug. 31, 2010

(54) MUTEIN OF A BONE MORPHOGENETIC PROTEIN AND USE THEREOF

(75) Inventors: Thomas Muller, Veitshochheim (DE); Walter Sebald, Würzburg (DE)

(73) Assignee: Julius-Maximilians-Universitat Wurzburg (DE)

( * ) Notice: Subject to any disclaimer, the term of this patent is extended or adjusted under 35 U.S.C. 154(b) by 698 days.

(21) Appl. No.: 10/591,482

(22) PCT Filed: Mar. 4, 2005

(86) PCT No.: PCT/EP2005/002328

§ 371 (c)(1), (2), (4) Date: Aug. 2, 2007

(87) PCT Pub. No.: WO2005/085281

PCT Pub. Date: Sep. 15, 2005

(65) Prior Publication Data

US 2007/0293425 A1 Dec. 20, 2007

(30) Foreign Application Priority Data

Mar. 4, 2004 (EP) ................................. 04005192

(51) Int. Cl.
*A61K 38/18* (2006.01)
*C07K 14/51* (2006.01)
(52) U.S. Cl. .......................................... 514/12; 530/350
(58) Field of Classification Search .................. None
See application file for complete search history.

(56) References Cited

U.S. PATENT DOCUMENTS

| | | | |
|---|---|---|---|
| 5,631,142 A * | 5/1997 | Wang et al. | ................ 435/69.1 |
| 5,965,403 A | 10/1999 | Celeste et al. | |
| 2002/0143170 A1 | 10/2002 | Ni et al. | |
| 2008/0119396 A1 | 5/2008 | Knopf et al. | |
| 2009/0042780 A1 | 2/2009 | Knopf et al. | |

FOREIGN PATENT DOCUMENTS

| | | |
|---|---|---|
| DE | 100 26 713 A1 | 12/2001 |
| EP | 0 704 532 A2 | 4/1996 |
| WO | WO-92/16228 A1 | 10/1992 |
| WO | WO-01/92298 A2 | 12/2001 |
| WO | WO-2005/085281 A1 | 9/2005 |

OTHER PUBLICATIONS

Andrades, J.A., et al., "A Recombinant Human TFG-β1 Fusion Protein with Collagen-Binding Domain Promotes Migration, Growth, and Differentiation of Bone Marrow Mesenchymal Cells," Experimental Cell Research, 250:485-498 (1999).
Balemans, W., et al., "Extracellular Regulation of BMP Signaling in Vertebrates: A Cocktail of Modulators," Developmental Biology, 250:231-250 (2002).
Bogan, A.A., et al., "Anatomy of Hot Spots in Protein Interfaces," J. Mol. Biol., 280:1-9 (1998).
Boulanger, M.J., et al., "Hexameric Structure and Assembly of the Interleukin-6/IL-6 α-Receptor/gp130 compLex," Science, 300:2101-2104 (2003).
Brunger, A.T., "Free R value: a novel statistical quantity for assessing the accuracy of crystal structures," Nature, 355:472-475 (1992).
Brunger, A.T., et al., "Crystallography & NMR System: A New Software Suite for Macromolecular Structure Determination," Acta Cryst., D54:905-921 (1998).
Chakrabarti, P., et al., "Dissecting Protein-Protein Recognition Sites," Proteins, 47:334-343 (2002).
Collaborative Computational Project, No. 4, "The CCP4 Suite: Programs for Protein Crystallography," Acta Cryst., D50:760-763 (1994).
Database NCBI Sequence Viewer, "Chain A, Structure of the Bone Morphogenetic Protein 2 Mutant L51p," Database Accession No. 1REUA (Nov. 7, 2003).
de Vos, A.M., et al., "Human growth hormone and extracellular domain of its receptor: crystal structure of the complex," Science, 255:306-312 (1992).
Evans, P.R., "Data reduction," Proceedings of CCP4 Study Weekend, pp. 114-122 (1993).
Greenwald, J., et al., "The BMP7/ActRII Extracellular Domain Complex Provides New Insights into the Cooperative Nature of Receptor Assembly," Mol. Cell., 11:605-617 (2003).
Groppe, J., et al., "Structural basis of BMP signalling inhibition by the cystine knot protein Noggin," Nature, 420:636-642 (2002).
Hage, T., et al., "Crystal Structure of the Interleukin-4/Receptor α Chain Complex Reveals a Mosaic Binding Interface," Cell, 97:271-281 (1999).
Hart, P.J., et al., "Crystal structure of the human TβR2 ectodomain-TGF-β3 complex," Nat. Struct. Biol., 9(3):203-208 (2002).
Kirsch, T., et al., "Isolation of recombinant BMP receptor IA ectodomain and its 2:1 complex with BMP-2," FEBS Letters, 468:215-219 (2000).
Kirsch, T., et al., "Crystal structure of the BMP-2-BRIA ectodomain complex," Nature Structural Biology, 7(6):492-496 (2000).
Kirsch, T., et al., "BMP-2 antagonists emerge from altercations in the low-affinity binding epitope for receptor BMPR-II," EMBO Journal, 19(13):3314-3324 (2000).
Leslie, A.G.W., "Recent changes to the MOSFLM package for processing film and image plate data," Joint CCP4+ESF-EAMCB Newsletter on Protein Crystallography, 26 (1992).
McDonald, I.K., et al., "Satisfying Hydrogen Bonding Potential in Proteins," J. Mol. Biol., 238:777-793 (1994).
Murshudov, G.N., et al., "Refinement of Macromolecular Structures by the Maximum-Likelihood Method," Acta Cryst., D53:240-255 (1997).
Nickel, J., et al. "The Crystal Structure of the BMP-2: BMPR-IA Complex and the Generation of BMP-2 Antagonists," Journal of Bone & Joint Surgery, 83-A(S1):S1-7 (2001).

(Continued)

*Primary Examiner*—David S Romeo
(74) *Attorney, Agent, or Firm*—Ropes & Gray LLP

(57) ABSTRACT

The present invention is related to a mutein of a bone morphogenetic protein, whereby the mutein comprises an amino acid substitution compared to the wildtype of the bone morphogenetic protein at the amino acid position corresponding to amino acid position 51 of human BMP-2.

22 Claims, 8 Drawing Sheets

OTHER PUBLICATIONS

Ruppert, R., et al., "Human bone morphogenetic protein 2 contains a heparin-binding site which modifies its biological activity," Eur. J. Biochem., 237:295-302 (1996).

Thompson, T.B., et al., "Structures of an ActRIIB:activin A complex reveal a novel binding mode for TGF-β ligand:receptor interactions," EMBO J., 22(7):1555-1566 (2003).

Tuan, T.L., et al., "Engineering, Expression and Renaturation of Targeted TFG-Beta Fusion Proteins," Connective Tissue Research, 34(1):1-9 (1996).

Winn, M.D., et al., "Use of TLS parameters to model anisotropic displacements in macromolecular refinement," Acta Cryst., D57:122-133 (2001).

Xu, D., et al., "Hydrogen bonds and salt bridges across protein-protein interfaces," Protein Eng., 10(9):999-1012 (1997).

Zhou, X., et al., "Nodal is a Novel TFG-β-like gene expressed in the mouse node during gastrulation," Nature, 361:543-547 (1993).

\* cited by examiner

MUTEIN OF A BONE MORPHOGENETIC PROTEIN AND USE THEREOF

The present invention is related to a mutein of a bone morphogenetic protein, nucleic acids coding therefor, methods for the production of such bone morphogenetic mutein, compositions, preferably pharmaceutical compositions comprising such mutein and the use of such mutein for the manufacture of a medicament.

The muteins according to the present invention are muteins of a bone morphogenetic protein. Bone morphogenetic proteins which are also referred to herein as BMP-2 like proteins, are one of two major groups forming the TGF-β superfamily. The other group of proteins belonging to said TGF-β superfamily apart from the BMP-2 like proteins are TGF-β-actin like proteins. The two groups of the TGF-β superfamily differ in their binding mechanisms. In general, the members of the TGF-β superfamily being structurally related polypeptide growth factors are involved in cellular processes, including cell proliferation, cell line determination, differentiation, mobility, adhesion and cell death. The factors are expressed according to a time and tissue specific pattern and are important for development, hemostasis and repair of nearly all tissues in eukaryotic organisms. These factors also account for an important part of intracellular signals which define the activity of a cell.

The signal transduction pathway of TGF-β has been elucidated in the more recent past. The signal transduction of TGF-β involves receptor serine kinases on the cell surface, and its substrates, namely the SMAD proteins, which are, upon phosphorylation migrating to the nucleus. The phosphorylated SMAD proteins activate transcription of the target gene in cooperation with DNA binding partners. The multifunctional activity of TGF-β and other members of the TGF-β superfamily seem to be based on the interaction of different receptors, SMAD proteins and DNA binding proteins. Any disturbance of this signal transduction pathway is the reason for a number of diseases in mammals and in man in particular. The members of the TGF-β superfamily share a number of structural features although the homology between said members is in some cases rather limited. For example, all of the proteins are dimers, typically are homodimers, i.e. comprised of two identical monomers. Also, the members of the TGF-β superfamily use cellular receptors which consist of two different types of serine kinase receptor chains, namely type I chain and type II chain.

The type I chain comprises a cytoplasmatic GS box and a serine kinase which activates SMAD-1 and SMAD-5 signal proteins if the type I chain is BRIA, BRIB or ARI. The type II chain activates a type I receptor serine kinase through phosphorylation of the GS box segment. The small receptor ecto domains of both the type I and type II chains, respectively, comprising about 120 to 150 amino acids only share a rather limited homology. Nevertheless, one common feature of all known receptor chains of the TGF-β superfamily are four conserved disulfide bridges; additional disulfide bridges and the position of some few amino acids seem to be characteristic for either type I or type II receptor proteins. The binding of BMP-2 like proteins to a type I chain occurs through the wrist epitope of the BMP-2 like proteins and to a type II chain through the "knuckle" epitope of the BMP-2 like proteins. The binding of these bone morphogenetic proteins to the respective receptor chains happens in a sequential manner at the cytoplasma membrane, whereby the particular sequence depends on the affinities of the bone morphogenetic protein to the individual receptor chains. For example, dissolved BMP-2 binds first to its high affinity type I chains, namely BMPR-IA, BMPR-IB and possibly also ActR-I, and subsequently assembles the low affinity type II receptor chain to form an active receptor complex. The assembling happens in the cytoplasma membrane.

Some amino acid substitutions in the wrist or in the knuckle epitope of BMP-2 result in inactive BMP-2 muteins which are no longer capable of activating the corresponding receptor. The inactive muteins which have the amino acid substitution in the knuckle epitope such as BMP-2 [A34D] are nevertheless able to bind to the type I chain similar to the wildtype BMP-2. However, the assembling of the type II chain in the membrane so as to form the active receptor complex comprising both the type I and type II chain is disturbed. Thus, this kind of muteins act as inhibitors of BMP-2 as they are competing with wildtype BMP-2 for the type I chain.

Apart from being involved in the signal transduction pathway involving a receptor comprising type I chains and type II chains, bone morphogenetic proteins and particularly BMP-2 like proteins interact with a group of modulator proteins. These modulator proteins are in turn involved in certain signal transduction pathways. Modulator proteins interacting with BMP-2-like proteins comprise, among others, members of the noggin protein family, the DAN protein family and the chordin protein family. These modulator proteins are known in the art and, for example, described in Avsian-Kretchmer, O. and Hsueh, A. J. (2004) Comparative genomic analysis of the eight-membered ring cystine knot-containing bone morphogenetic protein antagonists. Mol Endocrinol, 18, 1-12, which describes BMP-modulator proteins, more particularly cystine-knot-containing BMP-modulator proteins. The noggin family comprising, e.g., noggin, is described by Canalis, E., Economides, A. N. and Gazzerro, E. (2003) Bone morphogenetic proteins, their antagonists, and the skeleton. Endocr Rev, 24, 218-235; the chordin family comprising, among others, Chordin, Ventroptin, CTGF, CYR61, Crossveinless, Procollagen IIA, is, for example, described in Bork, P. (1993) The modular architecture of a new family of growth regulators related to connective tissue growth factor. FEBS Lett, 327, 125-130, Brigstock, D. R., Goldschmeding, R., Katsube, K. I., Lam, S. C., Lau, L. F., Lyons, K., Naus, C., Perbal, B., Riser, B., Takigawa, M. and Yeger, H. (2003) Proposal for a unified CCN nomenclature. Mol Pathol, 56, 127-128 and Garcia Abreu, J., Coffinier, C., Larrain, J., Oelgeschlager, M. and De Robertis, E. M. (2002) Chordin-like CR domains and the regulation of evolutionarily conserved extracellular signaling systems. Gene, 287, 39-47; and the DAN family comprising, for example Cerl, Cerberus, Dan, Dte, Gremlin, PRDC, Sclerostin is, e.g., described in Pearce, J. J., Penny, G. and Rossant, J. (1999) A mouse cerberus/Dan-related gene family. Dev Biol, 209, 98-110 and Balemans, W. and Van Hul, W. (2002) Extracellular regulation of BMP signaling in vertebrates: a cocktail of modulators. Dev Biol, 250, 231-250.

The problem underlying the present invention was thus to provide a mutein of bone morphogenetic proteins, particularly of BMP-2-like proteins which do not compete with the wildtype form of the respective bone morphogenetic proteins in terms of type I and type II serine kinase receptor chains mediated effects, but are still suitable to interact with modulator proteins such as those of the noggin protein family, the DAN protein family and the chordin protein family.

According to the present invention this problem is solved by the subject matter of the independent claims. Preferred embodiments may be taken from the dependent claims.

According to the present invention the problem is solved in a first aspect by a mutein of a bone morphogenetic protein, whereby the mutein comprises an amino acid substitution compared to the wildtype of the bone morphogenetic protein at the amino acid position corresponding to amino acid position 51 of human BMP-2.

In an embodiment the amino acid at the position corresponding to amino acid position 51 of human BMP-2 is leucine in the wildtype form of the bone morphogenetic protein and is preferably proline in the mutein.

In an embodiment the bone morphogenetic protein is selected from the group comprising hBMP-2, hBMP-4, hBMP-5, hBMP-6, hBMP-7, hBMP-8, hGDF-5, mGDF-6, mGDF-7, hBMP-10 and hGDF-2.

In an embodiment
  the bone morphogenetic protein is hBMP-2 and the position corresponding to amino acid position 51 of human BMP-2 is amino acid position 51;
  the bone morphogenetic protein is hBMP-4 and the position corresponding to amino acid position 51 of human BMP-2 is amino acid position 53;
  the bone morphogenetic protein is hBMP-5 and the position corresponding to amino acid position 51 of human BMP-2 is amino acid position 68;
  the bone morphogenetic protein is hBMP-6 and the position corresponding to amino acid position 51 of human BMP-2 is amino acid position 68;
  the bone morphogenetic protein is hBMP-7 and the position corresponding to amino acid position 51 of human BMP-2 is amino acid position 75;
  the bone morphogenetic protein is hBMP-8 and the position corresponding to amino acid position 51 of human BMP-2 is amino acid position 75;
  the bone morphogenetic protein is hGDF-5 and the position corresponding to amino acid position 51 of human BMP-2 is amino acid position 56;
  the bone morphogenetic protein is mGDF-6 and the position corresponding to amino acid position 51 of human BMP-2 is amino acid position 56;
  the bone morphogenetic protein is mGDF-7 and the position corresponding to amino acid position 51 of human BMP-2 is amino acid position 82;
  the bone morphogenetic protein is hBMP-10 and the position corresponding to amino acid position 51 of human BMP-2 is amino acid position 44; and
  the bone morphogenetic protein is hGDF-2 and the position corresponding to amino acid position 51 of human BMP-2 is amino acid position 45.

In an embodiment the wildtype of
  hBMP-2 comprises an amino acid sequence according to SEQ ID No. 1;
  hBMP-4 comprises an amino acid sequence according to SEQ ID No. 3;
  hBMP-5 comprises an amino acid sequence according to SEQ ID No. 5;
  hBMP-6 comprises an amino acid sequence according to SEQ ID No. 7;
  hBMP-7 comprises an amino acid sequence according to SEQ ID No. 9;
  hBMP-8 comprises an amino acid sequence according to SEQ ID No. 11;
  hGDF-5 comprises an amino acid sequence according to SEQ ID No. 13;
  mGDF-6 comprises an amino acid sequence according to SEQ ID No. 15;
  mGDF-7 comprises an amino acid sequence according to SEQ ID No. 17;
  hBMP-10 comprises an amino acid sequence according to SEQ ID No. 19; and
  hGDF-2 comprises an amino acid sequence according to SEQ ID No. 21.

In a preferred embodiment the wildtype of
  hBMP-2 is encoded by a nucleic acid according to SEQ ID No. 2;
  hBMP-4 is encoded by a nucleic acid according to SEQ ID No. 4;
  hBMP-5 is encoded by a nucleic acid according to SEQ ID No. 6;
  hBMP-6 is encoded by a nucleic acid according to SEQ ID No. 8;
  hBMP-7 is encoded by a nucleic acid according to SEQ ID No. 10;
  hBMP-8 is encoded by a nucleic acid according to SEQ ID No. 12;
  hGDF-5 is encoded by a nucleic acid according to SEQ ID No. 14;
  mGDF-6 is encoded by a nucleic acid according to SEQ ID No. 16;
  mGDF-7 is encoded by a nucleic acid according to SEQ ID No. 18;
  hBMP-10 is encoded by a nucleic acid according to SEQ ID No. 20; and
  hGDF-2 is encoded by a nucleic acid according to SEQ ID No. 22.

According to the present invention the problem is solved in a second aspect by a bone morphogenetic mutein, whereby the mutein is not binding to a first bone morphogenetic protein receptor and the mutein is binding to at least a modulator protein, whereby the modulator protein is selected from the group comprising the noggin protein family, the DAN protein family, the chordin protein family and the cysteine-knot-containing BMP modulator proteins.

According to the present invention the problem is solved in a third aspect by a bone morphogenetic mutein, which is preferably an embodiment of the first and the second aspect of the present invention, comprising a pre-helix loop structure which interacts with a bone morphogenetic protein receptor, preferably a second bone morphogenetic protein receptor. It is to be understood that the term second bone morphogenetic protein receptor is used in order to distinguish this kind of receptor from another receptor which is referred to herein as first bone morphogenetic protein receptor. This terminology is introduced herein for reasons of reference only and does not make allusion to the binding of the protein and mutein respectively. Insofar the binding of the protein and mutein, respectively, preferably occurs to a single bone morphogenetic protein receptor only. Such single bone morphogenetic protein receptor can be either the first bone morphogenetic protein receptor or the second bone morphogenetic protein receptor.

In an embodiment according to the second and the third aspect the bone morphogenetic mutein according to claim 7 and 8, whereby the first and/or the second bone morphogenetic protein receptor is BRIA or BRIB.

In an embodiment according to the second and the third aspect the interaction is related to an amino acid residue, preferably amino acid residue Gln86 of BRIA or Gln 67 of BRIB.

According to the present invention the problem is solved in a fourth aspect by a bone morphogenetic mutein, which is in a preferred embodiment a bone morphogenetic protein according to the first, second and third aspect, comprising a pre-helix loop structure having an interaction with a second bone morphogenetic protein receptor, whereby the interaction of the pre-helix loop structure of the bone morphogenetic mutein with the second bone morphogenetic protein receptor is different from the interaction of the pre-helix loop structure of the wildtype bone morphogenetic protein with the second bone morphogenetic protein receptor.

In an embodiment according to any aspect the different interaction or the change is represented in refraction data, preferably such refraction data being acquired at room temperature to a resolution of at least about 2.7 Å.

In an embodiment according to any aspect the pre-helix loop structure is mutated compared to the wildtype of the bone morphogenetic protein.

In an preferred embodiment the amino acid corresponding to leucine at position 51 of the wildtype BMP-2 is mutated.

In another preferred embodiment the amino acid corresponding to leucine at position 51 of human BMP-2 is mutated to proline.

In an embodiment according to any aspect the bone morphogenetic mutein is a mutein of a bone morphogenetic protein selected from the group comprising hBMP-2, hBMP-4, hBMP-5, hBMP-6, hBMP-7, hBMP-8, hGDF-5, mGDF-6, mGDF-7, hBMP-10 and hGDF-2.

In an preferred embodiment the bone morphogenetic protein is BMP-2 or pro-BMP-2.

According to the present invention the problem is solved in a fifth aspect by a bone morphogenetic protein comprising an amino acid sequence according to any of SEQ ID Nos. 23 to 33.

In an embodiment the bone morphogenetic mutein is a bone morphogenetic mutein according to any aspect of the present invention.

According to the present invention the problem is solved in a sixth aspect by a nucleic acid coding for a bone morphogenetic protein and bone morphogenetic mutein, respectively, according to any aspect of the present invention and/or a complementary strand thereto.

According to the present invention the problem is solved in a seventh aspect by a nucleic acid comprising a nucleic acid sequence according to SEQ ID Nos. 2, 4, 6, 8, 10, 12, 14, 16, 18, 20 and 22, preferably coding for a bone morphogenetic mutein according to any aspect of the present invention, and/or a complementary strand thereto.

According to the present invention the problem is solved in an eighth aspect by a nucleic acid coding for a bone morphogenetic mutein according to any aspect of the present invention, whereby the nucleic acid would hybridize to the nucleic acid according to the sixth and seventh aspect but for the degeneracy of the genetic code, more preferably under stringent conditions.

According to the present invention the problem is solved in a ninth aspect by a vector comprising a nucleic acid according to the sixth, seventh and eighth aspect, whereby the vector is preferably an expression vector.

According to the present invention the problem is solved in a tenth aspect by a cell, preferably a mammalian cell, comprising a nucleic acid according to the sixth, seventh and eighth aspect and/or a vector according to the tenth aspect of the present invention.

According to the present invention the problem is solved in an eleventh aspect by a host organism, preferably a mammalian host organism and more preferably a non-human host organism comprising a cell according to the tenth aspect of the present invention.

According to the present invention the problem is solved in a twelfth aspect by a method for the production of a bone morphogenetic mutein according to any of the first to fifth aspect of the present invention, comprising the steps of a) cultivating a cell according to claim 25 in a cultivation broth and b) preparing the bone morphogenetic mutein from the cell and/or from the cultivation broth.

According to the present invention the problem is solved in a thirteenth aspect by a monoclonal antibody specifically binding to a bone morphogenetic mutein according to any of the first to fifth aspect of the present invention.

According to the present invention the problem is solved in a fourteenth aspect by a composition comprising a mutein according to any of the first to fifth aspect and/or a nucleic acid according to any of the sixth to eighth aspect of the present invention.

According to the present invention the problem is solved in a fifteenth aspect by a pharmaceutical composition comprising a mutein according to any of the first to fifth aspect or a nucleic acid according to any of the sixth to eighth aspect of the present invention, and a pharmaceutically acceptable carrier.

According to the present invention the problem is solved in a sixteenth aspect by the use of a bone morphogenetic mutein according to any of the first to fifth aspect and/or of a nucleic acid according to any of the sixth to eighth aspect of the present invention, for the manufacture of a medicament.

In an embodiment the medicament is for the treatment and/or prevention of a disease selected from the group comprising fibrotic diseases, wound healing, hypervascularization, vascular diseases, fractures, and osteoporosis.

In a preferred embodiment the fibrotic disease is selected from the group comprising renal fibrosis, hepatic cirrhosis, pulmonary fibrosis and chronic inflammation, preferably chronic inflammation associated with asthma.

In another embodiment the wound healing is related to keloid, cicatrization, and peritoneal obliteration.

In a further embodiment the hypervascularization is related to or associated with retinopathies, arteriosclerosis and/or tumors.

In a still further embodiment the fractures are non-healing fractures.

In another embodiment the disease is osteoporosis.

According to the present invention the problem is solved in a seventeenth aspect by the use of a morphogenetic protein, preferably a morphogenetic mutein according to any of the first to fifth aspect of the present invention as inhibitor to a BMP interacting protein.

In an embodiment the BMP interacting protein is selected from the group comprising the noggin protein family, the DAN protein family and the chordin protein family.

The present inventors have surprisingly found that the muteins according to the present invention are capable of inhibiting the activity of modulator proteins such as those of the noggin family, the DAN family and the chordin protein family while not interacting with the receptor of the corresponding bone morphogenetic protein which is the bone morphogenetic protein based on which the proteins are generated by substituting at least one amino acid, more particularly the BMP-2-like protein receptor. Due to these characteristics of the muteins according to the present invention, they may be applied to any organism where said modulator proteins are to be modulated, preferably inhibited thus abolishing or decreasing the inhibition exerted by said modulator proteins, while the other biological activity related to the bone morphogenetic protein which is mediated through said receptor chains is no longer present. This design of a mutein of a bone morphogenetic protein is clearly advantageous insofar as it can be used in the treatment or prevention of said modulator protein related or mediated diseases without triggering the undesired receptor mediated effects of this kind of bone morphogenetic protein. Insofar the mutein according to the present invention is "receptor-dead".

Also, the present inventors have surprisingly found that this particular characteristic of the bone morphogenetic muteins can be created by changing the pre-helix loop structure in the bone morphogenetic protein in its wildtype form. As used herein and if not indicated to the contrary, a bone morphogenetic protein is preferably a BMP-2-like protein. The pre-helix loop structure is preferably the structure of a bone morphogenetic protein which is, preferably in a secondary structure representation, the loop preceding the helix of the bone morphogenetic mutein. Preferably, the loop comprises four to ten, preferably six to eight, more preferably six amino acid residues. Taking the amino acid sequence of the human BMP-2 protein, the pre-helix loop structure extends from amino acid position 48 to amino acid position 53. As used herein, in preferred embodiments the pre-helix loop is any loop, and more preferably any sequence of amino acids which correspond to amino acids 48 to 53 of the human BMP-2, more preferably of the amino acid sequence according to SEQ. ID. NO. 1. Preferably, the pre-helix loop structure is mediating the interaction with a bone morphogenetic protein receptor, which is preferably referred to herein as type I bone morphogenetic protein receptor. Even more preferably, the type I bone morphogenetic protein receptor is BRIA. $BRIA_{EC}$ is the extracellular domain of BMPR-IA and described in (see Kirsch, T., Sebald, W., Dreyer, M. K. (2000) Nat Struct Biol, 7, 492-496). $BRIB_{EC}$ is the extracellular domain of BMPR-IB. $ARI_{EC}$ is the extracellular domain of ActR-I.

The muteins according to the present invention are, due to the change in the structure, preferably secondary and tertiary structure as compared to the wildtype form of the bone morphogenetic protein no longer capable to interact with the type I bone morphogenetic protein receptor. The changes as preferably used herein, are those which are detectable by reference to the interaction of the wildtype form of the corresponding bone morphogenetic protein with said type I morphogenetic protein receptor. More particularly, it seems that in case of the type I bone morphogenetic protein receptor being the $BRIA_{EC}$ the amino acid mostly influenced by the mutein according to the present invention is Gln86.

Also, the bone morphogenetic mutein according to the present invention comprises a pre-helix loop structure which is mediating the interaction with a type I bone morphogenetic protein receptor such as $BRIA_{EC}$, whereby the interaction is different from the interaction of the pre-helix loop structure of the wildtype form of the bone morphogenetic protein with the type I bone morphogenetic protein receptor. Any of these induced changes or different interaction pattern between the mutein and the respective second bone morphogenetic protein receptor are detected relative to the corresponding structure or interaction of the wildtype form of the bone morphogenetic protein. Such changes of either or both of said type I bone morphogenetic protein receptor and of the mutein can preferably be monitored by acquiring refraction data. In a more preferred embodiment, such refraction data are acquired at room temperature to a resolution of at least about 2.7 Å.

In a preferred embodiment, the bone morphogenetic protein is BMP-2. BMP-2 is known in the art and preferably comprises the amino acid sequence according to SEQ ID No. 1 as described herein and is preferably encoded by a nucleic acid comprising a nucleic acid sequence according to SEQ ID No. 2.

More particularly, the present inventors have also discovered that the particular characteristics of the muteins according to the present invention are conferred by an amino acid substitution, i.e. mutation, at the pre-helix loop structure, more particularly at the amino acid position of the bone morphogenetic proteins, preferably of the BMP-2 like proteins which corresponds to amino acid position 51 of human BMP-2, more preferably of the BMP-2 according to SEQ. ID. NO. 1. More particularly, the respective amino acid which is mutated in the mutein is the leucine in the corresponding wildtype forms of the bone morphogenetic proteins. More preferably, the exchange is from a leucine residue to a proline residue. Due to the high homology and thus similar secondary and tertiary structure of the bone morphogenetic proteins, particularly of the BMP-2-like proteins, the particular position is similarly active and relevant, respectively, within the various members of this group of bone morphogenetic proteins so that the change, i.e. amino acid substitution is effective in any of said bone morphogenetic proteins and, thus, the respective muteins exhibit the characteristics outlined above. More preferably, the bone morphogenetic proteins are hBMP-2, hBMP-4, hBMP-5, hBMP-6, hBMP-7, hBMP-8, hGDF-5, mGDF-6, mGDF-7, hBMP-10 and hGDF-2 which are as such known in the art and all of which bind in a similar manner to $BRIA_{EC}$. However, the respective mutation turning them into corresponding muteins, i.e. having an amino acid substitution at their positions corresponding to amino acid position 51 of human BMP-2 distinguishes them from the prior art. The wildtype sequences of the aforementioned bone morphogenetic proteins are disclosed herein as SEQ ID No. 1 (hBMP-2), SEQ ID No. 3 (hBMP-4), SEQ ID No. 5 (hBMP-5), SEQ ID No. 7 (hBMP-6), SEQ ID No. 9 (hBMP-7), SEQ ID No. 11 (hBMP-8), SEQ ID No. 13 (hGDF-5), SEQ ID No. 15 (mGDF-6), SEQ ID No. 17 (mGDF-7), SEQ ID No. 19 (hBMP-10) and SEQ ID No. 21 (hGDF-2), whereby the corresponding amino acid sequences of the inventive muteins of said bone morphogenetic proteins differ in said single amino acid position compared to the wildtype and said amino acid sequences are those according to SEQ ID No. 23 (hBMP-2), SEQ ID No. 24 (hBMP-4), SEQ ID No. 25 (hBMP-5), SEQ ID No. 26 (hBMP-6), SEQ ID No. 27 (hBMP-7), SEQ ID No. 28 (hBMP-8), SEQ ID No. 29 (hGDF-5), SEQ ID No. 30 (mGDF-6), SEQ ID No. 31 (mGDF-7), SEQ ID No. 32 (hBMP-10) and SEQ ID No. 33 (hGDF-2). More particularly, said amino acid position 51 of human BMP-2 corresponds to position 53 in case of hBMP-4, to position 68 in case of hBMP-5, to position 68 in case of hBMP-6, to position 75 in case of hBMP-7, to position 75 in case of hBMP-8, to position 56 in case of hGDF-5, to position 56 in case of mGDF-6, to position 82 in case of mGDF-7, to position 44 in case of hBMP-10, and to position 45 in case of hGDF-2.

As used herein, a bone morphogenetic protein and thus the corresponding mutein which differs therefrom preferably only by the single amino acid substitution disclosed herein, can be present in the pre-pro-form, in the pro-form or as mature protein. This basic design is inherent to all of the bone morphogenetic proteins. In case of BMP-2, for example, the pre-pro-form comprises a total of 396 amino acids. The pre-sequence serves as a signal peptide and is responsible for the transport of the nascent polypeptide chain into the endoplasmatic reticulum. After importation the protein folds into its native confirmation, whereupon disulfide bridges are formed. The pro-form of BMP-2 comprises all of the amino acids from position 20 to position 396. Accordingly, the pro-sequence comprises the amino acids from position 20 (Gly) to amino acid position 282 (Arg) of the human pre-pro-form of BMP-2. Finally, the mature BMP-2 comprises amino acids 283 to 396 of the pre-pro-form. The mature form is depicted herein also as SEQ ID No. 1.

It is within the present invention that the bone morphogenetic proteins and their corresponding muteins according to the present invention are present in the pre-pro-form, in the pro-form or in the mature form, whereby any signal peptide may act as pre-sequence, preferably of a bone morphogenetic protein, and any pro-sequence of any bone morphogenetic protein can be used as the pro-sequence of the particular bone morphogenetic protein, although it is more preferred that the pro-sequence attached to the N-terminus of the mature bone morphogenetic muteins correspond to the one attached to the N-terminus of the respective bone morphogenetic protein in vivo. The same also applies to the pre-sequence.

The term "bone morphogenetic protein" and "bone morphogenetic mutein", respectively, as preferably used herein, also comprises orthologues thereof. As used herein, an orthologue is a protein from another organism that fulfills the same genetic and physiological function as the reference protein. Also, in a more preferred embodiment, the term "bone morphogenetic protein" and "bone morphogenetic mutein" comprises any truncated protein and mutein, respectively. Preferably, such truncated protein and mutein lacks at least one amino acid residue, preferably at either the N terminus or the C terminus. Preferably the mutein lacks at least one domain. A bone morphogenetic mutein according to the present invention is thus also a truncated mutein as long as it still exhibits the characteristics outlined above, i.e. being "receptor-dead" and still suitable to interact with at least one modulator proteins, preferably a member of the noggin protein family, the DAN protein family and/or the chordin protein family.

It is also within the present invention that the mutein is further modified whereby such modification is preferably selected from the group comprising phosphorylation, pegylation and glycosylation.

It is to be understood that any of the nucleic acids according to the present invention can be present as DNA, RNA or any derivative thereof such as LNA or PNA. It is also within the present invention that the respective nucleic acid is present as a single strand or a double strand, either partially or completely. Finally, it is within the present invention that the term "nucleic acid sequence" also comprises the complement of such nucleic acid specified, for example as specified by the sequence according to a sequence identifiers, either alone or in combination with the other, essentially complementary strand.

The term "nucleic acid" as used herein also comprises any fragments of the nucleic acid as described herein, whereby preferably any such fragment comprises a length from about 19 to 30, more preferably 19 to 25 and most preferably 21 and 22 consecutive nucleotides. Even more preferably this kind of fragment of a nucleic acid is present as a double-stranded structure.

According to the present invention, the nucleic acid can also be a nucleic acid which hybridizes to any other form of nucleic acid disclosed herein, whereby such hybridization preferably occurs at stringent conditions. Such stringent conditions are, among others, described in Sambrook, J., Fritsch, E. F. and Maniatis, T. (1989) Molecular Cloning. A. Laboratory Manual, $2^{nd}$ ed. pp. 9.47-9.55, Cold Spring Harbour Laboratory Press.

It will be acknowledged by the ones skilled in the art that starting from either the wildtype sequence of the bone morphogenetic protein or of the mutein thereof as described herein, it is possible to design a nucleic acid which is able to discriminate between the wildtype form of the bone morphogenetic protein and the mutein thereof. Preferably such discrimination is possible by increasing the stringency of the hybridization conditions.

It is also to be acknowledged by the ones skilled in the art that apart from the particular sequences disclosed herein, also different sequences, more preferably nucleic acid sequences, are comprised by the present invention as long as they are suitable to code for the muteins according to the present invention. Such sequence can be derived using the genetic code and factually any permutation of such sequence which arises due to the redundancy of the genetic code is within the present invention. About the particular amino acid substitution which is characteristic to the muteins according to the present invention where at the position of the bone morphogenetic proteins and muteins, respectively, corresponding to amino acid position 51 of human BMP-2 being proline rather than leucine it is to be acknowledged that the respective codon can be CCU, CCC, CCA or CCG.

The vector according to the present invention contains any of the nucleic acids as disclosed herein, including any of the fragments disclosed herein. Preferably, the vector is an expression vector. Such expression vector typically comprises a promotor or promotor-like structure and optionally further elements which are suitable to control the expression of the nucleic acid cloned into the vector such as to be controlled by such promotor and other controlling elements. Preferably, the expression vector is a prokaryotic expression vector or an eukaryotic expression vector or a respective shuttle vector. The particular design of expression vectors of this type is known to the ones skilled in the art.

The cell according to the present invention is either a prokaryotic cell or an eukaryotic cell. As prokaryotic cell, in principle, *E. coli*, *B. subtilis* or *S. carnosus*, is used for the expression of the nucleic acid coding for a bone morphogenetic mutein according to the present invention, or a fragment or derivative thereof.

An eukaryotic cell as used herein is preferably a yeast cell or a mammalian cell. More preferably, the mammalian cell is a cell from mouse, rat, guinea-pig, pig, monkey or human being.

The host organism as used herein is preferably any of the cells according to the present invention or a multi-cellular organism. Such multi-cellular organism is preferably a mammal, more preferably a non-human mammalian. A preferred non-human mammal is selected from the group comprising mouse, rat, guinea-pig, sheep, rabbit and pig.

In the method according to the present invention for the production of a bone morphogenetic mutein according to the present invention, preferably a cell according to the invention is cultivated. Such cultivation is preferably performed in a cultivation broth. A cultivation broth is preferably a fermentation broth or any other solution which is suitable for the cultivation and more preferably for the propagation of the cell to be cultivated. Cultivation broths are known to the ones skilled in the art. Preferably upon cultivation and/or propagation of the cell the muteins according to the present invention may be prepared from the cultivation broth. Preparation from the cultivation broth, as used herein, comprises the preparation from the cell which may contain the mutein according to the present invention either intracellularly or otherwise attached to the cell, or may comprise the isolation or preparation of the mutein according to the present invention from the cultivation broth. Methods for preparing or isolating the mutein according to the present invention are known to the ones skilled in the art.

In a further aspect the present invention is related to a monoclonal antibody which is directed against a mutein according to the present invention. Preferably, the antibody is a monoclonal antibody. It is to be acknowledged by the one skilled in the art that it is possible to prepare an antibody, preferably a monoclonal antibody which is specifically binding to a bone morphogenetic mutein according to the present invention.

Preferably, the term "specifically binding" means that the antibody is not binding to the wildtype form of the bone morphogenetic protein to the same extent or following the same binding characteristics as to the mutein, whereby at least the binding constant of the mutein compared to the corresponding wildtype form of the bone morphogenetic protein differs by a factor of at least 2, preferably by a factor of at least 5 and most preferably by a factor of at least 10.

In a further aspect the present invention is related to a composition comprising either a mutein according to the present invention or a nucleic acid according to the present invention. Such composition may comprise apart from the protein and/or the nucleic acid a carrier. Preferably such carrier is selected from the group comprising solid phases, aqueous phases and lipid phases. Lipid phases as used herein are preferably lipids or a lipid compositions complexing or encompassing the nucleic acid and the mutein, respectively. Preferred lipid compositions insofar are liposomes as known to the ones skilled in the art. Aqueous phases are preferably selected from the group comprising water and aqueous buffer solutions and hyaluronic acid. Solid phases are preferably tricalcium phosphat, polylactides, collagen and insoluble collagen bone matrix.

In a further aspect the present invention is related to a pharmaceutical composition. Such pharmaceutical composition comprises a mutein according to the present invention or a nucleic acid according to the present invention, or both, in addition to a pharmaceutically acceptable carrier. A pharmaceutically acceptable carrier is preferably either a liquid or a solid carrier. Suitable liquid carriers are, among others, water, aqueous solutions, more preferably buffers, or lipids or lipid compositions. Preferred solid carriers comprise, among others, sugar, cellulose and starch. It is to be acknowledged that those skilled in the art, preferably in the art of formulations, are aware of further pharmaceutically acceptable carriers and carrier material, respectively. In a preferred embodiment the pharmaceutical composition comprises a further pharmaceutically active agent.

In a further aspect the present invention is related to the use of a bone morphogenetic mutein according to the present invention and/or of a nucleic acid according to the present invention for the manufacture of a medicament.

It will be acknowledged by the ones skilled in the art that based on the surprising findings of the present inventors, namely that the muteins of bone morphogenetic proteins and more particularly of BMP-2 like proteins according to the present invention do not exhibit the receptor mediated effects of such bone morphogenetic proteins, i.e. and are thus "receptor-dead", while still interacting with the modulator proteins with which the wildtype form of the respective bone morphogenetic protein interact. Insofar, the muteins according to the present invention and nucleic acids coding therefor, can be applied to a patient in need thereof without running into the risk that the known undesired effects of bone morphogenetic proteins will occur, thus outweighing the benefits of interacting with the modulator proteins inhibiting their inhibitory activity. For example, undesired activities of BMP-2 are, among others, promoting tumor growth. Because of this, the medical use of bone morphogenetic proteins, including any muteins thereof of the prior art, has been limited to local administration such as in bone regeneration. However, the muteins according to the present invention being devoid of those effects of bone morphogenetic protein activities particularly mediated through the interaction with their receptors allow for the very first time the medical application of this class of pharmaceutically active compounds.

A further aspect of the present invention is related to a method for the treatment of a patient suffering from or being in a condition to develop any of the diseases described herein for which the medicament according to the present invention may be used. Such method comprises the administration of a mutein or a nucleic acid coding therefor, to the patient. Preferably, the patient is a mammal, more preferably the patient is a human being.

Due to the mode of action of the muteins according to the present invention, they can be readily used for various diseases, namely those diseases which can be treated or prevented by providing for an undisturbed interaction between the bone morphogenetic proteins and corresponding muteins according to the present invention, and any modulator proteins. Preferably, the modulator proteins are known in the art and are selected from the group comprising cystine knot-containing bone morphogenetic proteins, more particularly the cystine knot-containing BMP modulator proteins, the noggin family, the chordin family, and the DAN family. The cystine knot-containing BMP modulator proteins are, for example, described in Avsian-Kretchmer, O. and Hsueh, A. J. (2004) Comparative genomic analysis of the eight-membered ring cystine knot-containing bone morphogenetic protein antagonists. Mol Endocrinol, 18, 1-12. The noggin family comprising, e.g., noggin, is described by Canalis, E., Economides, A. N. and Gazzerro, E. (2003) Bone morphogenetic proteins, their antagonists, and the skeleton. Endocr Rev, 24, 218-235; the chordin family comprising, among others, Chordin, Ventroptin, CTGF, CYR61, Crossveinless, Procollagen IIA, is, for example, described in Bork, P. (1993) The modular architecture of a new family of growth regulators related to connective tissue growth factor. FEBS Lett, 327, 125-130, Brigstock, D. R., Goldschmeding, R., Katsube, K. I., Lam, S. C., Lau, L. F., Lyons, K., Naus, C., Perbal, B., Riser, B., Takigawa, M. and Yeger, H. (2003) Proposal for a unified CCN nomenclature. Mol Pathol, 56, 127-128 and Garcia Abreu, J., Coffinier, C., Larrain, J., Oelgeschlager, M. and De Robertis, E. M. (2002) Chordin-like CR domains and the regulation of evolutionarily conserved extracellular signaling systems. Gene, 287, 39-47; and the DAN family comprising, for example, Cerl, Cerberus, Dan, Dte, Gremlin, PRDC, Sclerostin is, e.g., described in Pearce, J. J., Penny, G. and Rossant, J. (1999) A mouse cerberus/Dan-related gene family. Dev Biol, 209, 98-110 and Balemans, W. and Van Hul, W. (2002) Extracellular regulation of BMP signaling in vertebrates: a cocktail of modulators. Dev Biol, 250, 231-250. It is to be acknowledged that these modulator proteins are known to have an inhibitory or stimulatory effect on pathways and events in a cell which, when biased, particularly when not inhibited themselves, tend to have an inhibitory effect on in vivo processes resulting in some diseases or a diseased condition. Therefore, without wishing to be bound by any theory, the muteins according to the present invention which may still interact with said modulator proteins and can thus inhibit their modulatory effect allowing that the process otherwise inhibited or stimulated by the modulator proteins can be performed at all or at a higher or lower level compared to the extent observed in the presence of the modulator proteins alone.

Particularly preferred diseases which can be treated by the muteins and the nucleic acids coding therefor, according to the present invention are fibrotic diseases. Particularly preferred diseases which may be treated according to the present invention are renal fibrosis, hepatic cirrhosis, pulmonary fibrosis and chronic inflammation, more preferably chronic inflammation associated with asthma and, therefore, also the treatment of asthma is comprised by the present invention.

Again without wishing to be bound by any theory, CTGF belonging to the Chordin-family interacts with BMP-2 and thus with the muteins according to the present invention. CTGF is mediating a pro-fibrotic activity of TGF-β. More particularly, TGF-β is stimulating the production of proteins of the extracellular matrix and inhibits the degradation of this kind of proteins. Normally, this process is an integral part of the healing of tissue. In case of chronic diseases, however, such as inflammatory diseases and more particularly chronic inflammation, TGF-β activity is exuberant thus leading to tissue fibrosis, particularly excessive tissue fibrosis (Branton, M. H. and Kopp, J. B. (1999) TGF-beta and fibrosis. Microbes Infect, 1, 1349-1365). These various fibrotic diseases can thus be inhibited by the administration of a mutein according to the present invention.

A further kind of diseases which may be treated according to the present invention is wound healing. More preferably, the form of this medical condition, i.e. wound healing, are keloid, cicatrization, and peritoneal obliteration. A particular group of patients which can be treated according to the present invention are patients who undergo or have undergone a glaucoma surgery which preferably goes along with intense cicatrization affecting eye vision. Again, without wishing to be bound by any rational, the exuberant cicatrization seems to be mediated through CTGF and CYR61 (Branton, M. H. and Kopp, J. B. (1999) TGF-beta and fibrosis. Microbes Infect, 1, 1349-1365) so that an inhibition of these modulator proteins through the muteins according to the present invention is a suitable means to avoid cicatrization and thus to treat the respective condition and disease, respectively.

Another disease or condition to be treated according to the present invention is hypervascularization. More particularly, the term "hypervascularization" comprises any disease which is caused, related to or associated with hypervascularization. Preferably this kind of diseases are tumors, retinopathies and arteriosclerosis. Insofar the present invention is also related to the use of the muteins according to the present invention for the treatment of tumors, retinopathies. Preferably, the tumors are solid tumors. Also, vascular diseases, such as preferably arteriosclerosis, can be treated according to the present invention. Again, without wishing to be bound by any theory it seems that solid tumors require a sufficient vascularization in case they grow beyond a volume of 1 to 3 mm³. A sufficient blood supply is a limiting step during growth and progression of a tumor. According to the current understanding of the present inventors, CYR61 is involved in tumor angiogenesis. More particularly, CYR61 and CTGF, respectively, are understood as being involved in angiogenic and fibrogenous progresses which are involved in progressive vascular occlusion (Brigstock, D. R. (2002) Regulation of angiogenesis and endothelial cell function by connective tissue growth factor (CTGF) and cysteine-rich 61 (CYR61), Angiogenesis, 5, 153-165). Thus by interacting with said target molecules, i.e. CYR61 and CTGF, the muteins according to the present invention are suitable for the prevention and treatment of the respective diseases.

A further disease and condition, respectively, which can be treated according to the present invention are fractures, preferably non-healing fractures. Again without wishing to be bound by any theory it seems that noggin and CTGF are BMP-modulating proteins involved in the healing of fractures. More particularly, noggin and CTGF inhibit and terminate bone formation (Yoshimura, Y., et al., (2001), Colocalization of noggin and bone morphogenetic protein-4 during fracture healing, J Bone Miner Res, 16, 876-884). Thus inhibiting the effect of noggin and CTGF by, for example, competitive inhibition with the interaction partners of said targets, the muteins according to the present invention affect a treatment of this condition.

Osteoporosis is another disease which can be treated according to the present invention. Again without wishing to be bound by any theory, it seems that in connection with this disease the target is sclerostin. Sclerostin inhibits the bone forming processes in an organism. People suffering from an inactivation of the sclerostin gene (SOST) show a continuous increase in bone density which may reach up to three times of the standard value. Insofar any compound inhibiting sclerostin would be a suitable means for the treatment of conditions going along with reduced bone density such as, for example, osteoporosis (Balemans, W. and Van Hul, W. (2002), Extracellular regulation of BMP signaling in vertebrates: a cocktail of modulators, Dev Biol, 250, 231-250). Insofar given the fact that the muteins according to the present invention interact with sclerostin and thus inhibit this compound, they are suitable for the treatment of this kind of diseases and conditions, respectively, more preferably of osteoporosis.

The present invention is further illustrated by the figures and examples from which further features, embodiments and advantages may be taken, wherein FIG. 1 (A) shows a ribbon sketch of the complex structure of BMP-2 and $BRIA_{EC}$;

FIG. 1 (C) shows a surface representation of the interface of BMP-2 and $BRIA_{EC}$;

Figure 7:
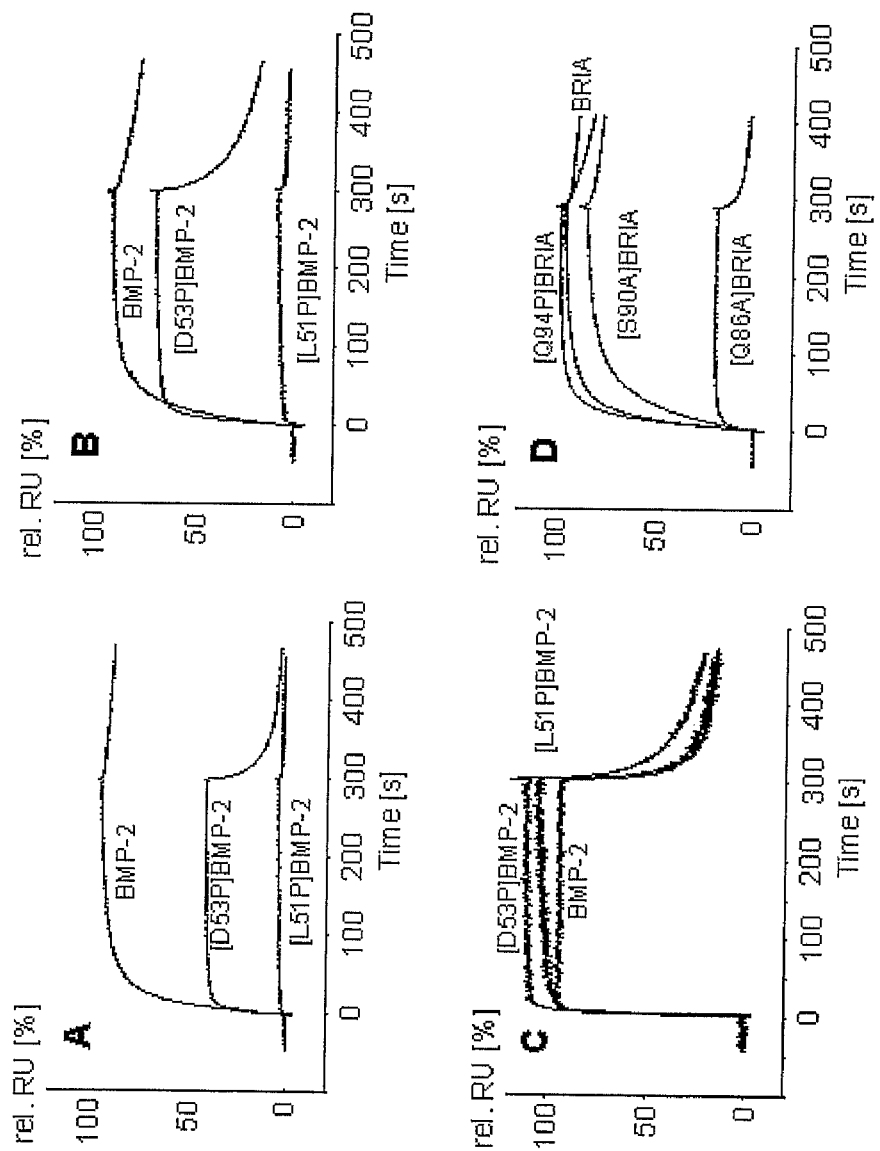
Figure 8:
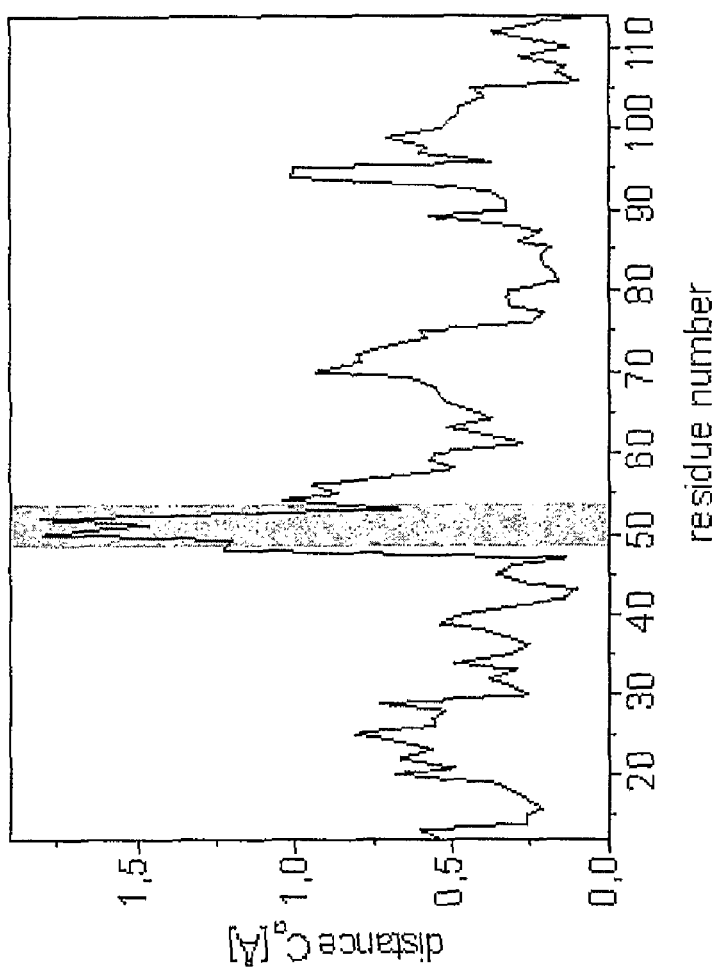

FIG. 7 shows sensograms of the interaction between BMP proline muteins and (A) $BRIA_{EC}$, (B) $BRIB_{EC}$, or (C) Activin receptor II ectodomain and (D) interaction between BMP-2 and $BRIA_{EC}$ muteins, whereby all ligands were present at 120 nM concentration and the sensograms were normalized by setting resonance units (RU) calculated for saturating analyte BMP-2 concentration as 100%; and FIG. 8 shows structural differences between BMP-2 wild type and BMP-2 L51P, whereby the $C_\alpha$-atoms of both structures were superimposed and the in-between distances are shown and the region for the pre-helix loop is highlighted in grey.

EXAMPLE 1

Materials and Methods

Preparation of Proteins

Preparation of BMP-2 mutein and BMP receptor ectodomain proteins was performed as described previously (Kirsch et al., 2000b; Ruppert et al., 1996). Variants for BMP-2 or $BRIA_{EC}$ were obtained by recombinant PCR (Kirsch et al., 2000a). BMP-2 wildtype and mutein protein used for crystallization was purified by cation exchange chromatography using an EMD $SO_3^-$ column (Merck). Fractions were analyzed by SDS-PAGE and pooled fractions were dialyzed against water and freeze-dried. Homogeneity of the proteins was checked by ESI FT-CR mass spectroscopy and analytical reversed-phase HPLC. Binding activity of the refolded BMP-2 muteins was assessed by measurement of the binding affinity for BMP type I and II receptor using BIAcore methodology. Preparation of the BMP-2-BRIA$_{EC}$ complex for structure analysis was performed as published (Kirsch et al., 2000b).

Crystallisation of the Proteins

For crystallisation, BMP-2 D53P and BMP-2 L51P were dissolved in water at a concentration of 5 and 8 mg ml$^{-1}$, respectively. BMP-2 L51P was crystallised by the hanging drop vapour diffusion method at room temperature from 15% t-butanol, 0.1 M lithium sulphate and 0.1 M sodium citrate pH 5.0. Crystallisation of the complex of BMP-2-BRIA$_{EC}$ was performed basically as published (Kirsch et al., 2000b) however crystals for measurement at 100 K were obtained by co-crystallizing using glucose as cryo-protectant. High quality crystals for data acquisition grew from 0.75 M sodium acetate, 0.1 M imidazole pH 7.0 and 30% glucose at 10° C. using a protein concentration of 11 mg ml$^{-1}$.

X-Ray Data Acquisition

Data for the complex of BMP-2-BRIA$_{EC}$ were obtained from a single crystal at 100 K at the beamline X06SA PX at the Swiss Light Source (Paul Scherrer Institute, Switzerland). Two datasets with 90° rotation of the crystal (1° per frame) were measured, a high-resolution set with 10 s exposure for 1° yielded a maximum resolution of 1.9 Å, low-resolution data was obtained by recording with 1 s exposure time per degree. The data were processed and integrated using the software MOSFLM version 6.2.1 (Leslie, 1992), the two datasets were merged (overlap: 20-5.0 Å for low-resolution, 20-1.9 Å for high-resolution) and scaled using the software SCALA CCP4 version 4.2.1 (Collaborative Computational Project, 1994; Evans, 1993), a summary for the processing statistics is given in table A supplement. Diffraction data for the BMP-2 mutein L51P were acquired at room temperature on a home-source consisting of a Rigaku RU-300 (50 kV, 100 mA, 0.3 mm filament), Osmic ConfocalBlue optics and a Rigaku R-AXIS IV++ imageplate system. The exposure time was set to 5 min per 0.5° rotation, crystals diffracted up to 2.5 Å. An acquisition strategy was determined using the software CrystalClear (Rigaku) to minimize radiation damage, however to realize reasonable completeness, data from two crystals was collected, merged and scaled using the software MOSFLM and SCALA (Evans, 1993; Leslie, 1992).

Structure Determination

The structure of the complex of BMP-2-BRIA$_{EC}$ was refined by using the lower resolution structure (PDB entry 1ES7) as a start model. The BMP-2-BRIA$_{EC}$ complex crystallises in the space group P6$_5$, with the asymmetric unit holding a BMP-2 dimer and two BRIA$_{EC}$ molecules. Due to slight changes in the cell constants, a molecular replacement step consisting of a rotation and translation search followed by a rigid body refinement was performed using the software CNS 1.1 (Brunger et al., 1998). The program REFMAC5 (Murshudov et al., 1997) was subsequently used for refinement followed by manual rebuilding of the coordinates using the software QUANTA2000 (Accelrys). The resolution was gradually increased to a final resolution range of 20 to 1.9 Å. One TLS group was defined for each chain, i.e. BMP-2 monomers and each BRIA$_{EC}$ molecule to account for anisotropy in the data (Winn et al., 2001). The progress of refinement was monitored by cross-validation using a test data set comprising of 5% of the reflections (Brunger, 1992). Since the complex structure is principally symmetrical, we tried to employ non-crystallographic symmetry restraints, however in the subsequent refinement steps the R$_{free}$ could not be lowered without the NCS restraints being violated. Therefore, no NCS restraints were used throughout the refinement. In the final round of refinement f$_{obs}$-f$_{calc}$ difference electron density maps were used to identify 185 water molecules. The final minimization cycle yielded an R-factor of 20.7 and 22.9 for R$_{free}$. The structure analysis of BMP-2 L51P followed the protocol for the BMP-2-BRIA$_{EC}$ complex however CNS 1.1 was used for simulated annealing and energy minimization. The structure of BMP-2 wild type (PDB entry 3BMP) served as a start model. Manual rebuilding of the model was based on $\sigma_A$-weighted 2f$_{obs}$-f$_{calc}$ and f$_{obs}$-f$_{calc}$ electron density maps, in the final round of refinement 13 water and two MPD molecules were added. The R-factor for the final structure of BMP-2 L51P is 21.5 and 23.5 for R$_{free}$.

Interaction Analysis

Proteins were biotinylated and immobilised to streptavidin-coated sensor chip CM5 (Kirsch et al., 2000a). The extracellular domain of BRIA, BRIB and ARII were prepared as described (Kirsch et al., 2000a). Noggin/Fc, Chordin and Gremlin were obtained from R&D systems (Wiesbaden-Nordenstadt). Interaction with analyte was measured on a BIAcore 2000 system (Kirsch et al., 2000a). Evaluation of sensorgrams (Biaevaluation software 2.0) yielded kinetic constants for complex formation (k$_{on}$) and dissociation (k$_{off}$). 6 to 12 measurements yielded mean values with a mean standard deviation of 35% for k$_{off}$ and 12% for k$_{on}$. Apparent dissociation constants K$_D$ were either calculated as K$_D$=k$_{off}$/k$_{on}$ or by evaluating dose dependency of equilibrium binding. Special conditions had to be applied to regenerate free Noggin after BMP-2 binding. The remaining complex could be only dissociated at acidic pH 3 in the presence of 1 M sodium chloride and 6 M Urea. Fortunately, the protein retained native binding properties after this harsh treatment as established by independent single cycle experiments employing immobilisation of the Noggin-Fc fusion protein to sensor-fixed protein A.

Biological Activity in Cell Lines

Alkaline phosphatase (ALP) activity was determined in serum-starved ATDC5 (Riken Bioresource Center, Cell number RCB0565) and C2C12 (ATCC Number CRL-1772) cells (Kirsch et al., 2000a).

EXAMPLE 2

Hydrogen Bonding Pattern in the BMP-2-BRIA$_{EC}$ Complex

Figure 1:
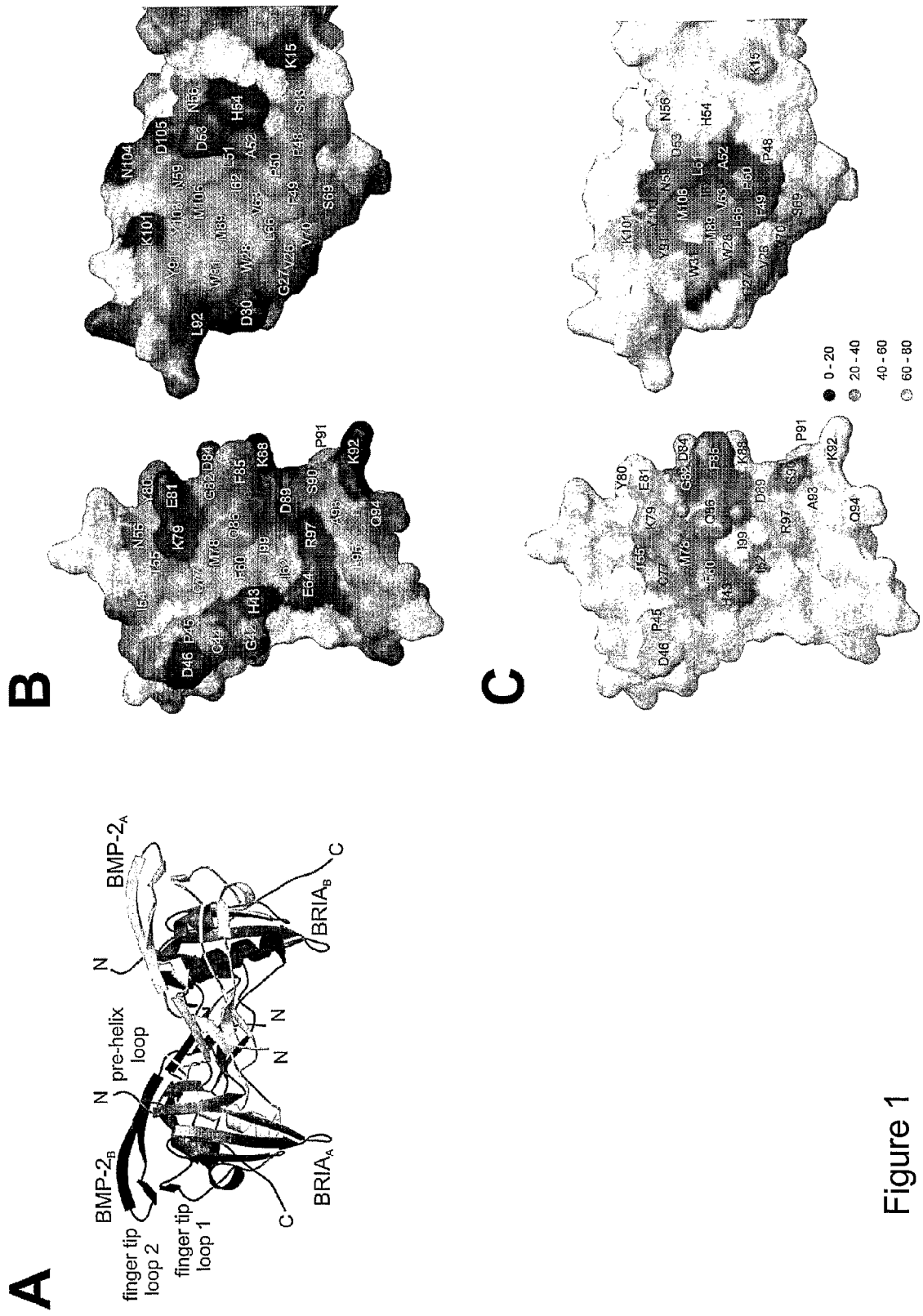
FIG. 1 (B) shows a surface representation in an "open book" view with the receptor BRIA being rotated 180° around the y-axis, of the interface of BMP-2 and $BRIA_{EC}$.

The high resolution structure of the BMP-2-BRIA$_{EC}$ complex contains one complete BMP-2 dimer bound to two BRIA ectodomains in the asymmetric unit (FIG. 1A). Applying strict non-crystallographic symmetry failed showing that the symmetry of the ligand-receptor complex is not perfect. However, differences between the two segments (BMP-2 dimer and one BRIA$_{EC}$ molecule) are small with an r.m.s. deviation of 0.9 Å for all atoms and 0.4 Å for all C$_\alpha$-atoms. A detailed analysis shows that the structure of the two BMP-2/BRIA$_{EC}$ interfaces is the same. All dissimilarities between the non-crystallographic symmetry related molecules are due to differences in the packing environment in the crystal lattice. The high temperature factor in these segments suggests that all the differences might be due to backbone flexibility. Thus, structural variations in the symmetry-related protein segments do not reflect real dissimilarities between the individual molecules but rather possible conformations and dynamics of the BMP-2 and BRIA polypeptide chains.

The BMP-2/BRIA interface represents a new paradigm for a growth factor/receptor interface. The binding epitope of BMP-2 is highly hydrophobic with almost 60% of the total buried surface area of 2310 Å$^2$ built by hydrophobic residues (FIG. 1b). Compared with binding epitopes of other growth factors, like human growth hormone (de Vos et al., 1992), interleukin-4 (Hage et al., 1999), erythropoietin (Syed et al., 1998) or interleukin-6 (Boulanger et al., 2003), this level of hydrophobicity is quite high. An extremely hydrophobic contact side seems to be characteristic for members of the TGF-β superfamily, as shown in the complex structures of BMP-7 bound to Activin receptor II ectodomain (Greenwald et al., 2003), TGF-β3 in complex with TGF-β receptor II (Hart et al., 2002), and Activin A bound to Activin receptor IIB (Thompson et al., 2003). In contrast, the binding epitope of BRIA$_{EC}$ is much less hydrophobic (30%) due to a stretch of polar and charged residues running across the binding interface (FIG. 1B).

The higher resolution of 1.9 Å of the refined structure of the BMP-2-BRIA$_{EC}$ complex allows for a more detailed analysis as was possible for the previous structure at lower resolution. In each BMP-2/receptor interface 10 intermolecular hydrogen bonds (H-bonds) are identified by the program HBPLUS (McDonald and Thornton, 1994) (Table 1). BMP-2 provides 5 and the receptor 4 main chain atoms to hydrogen bonding. The atoms engaged in H-bonds cluster into two structural elements as depicted in table 1: on the ligand BMP-2 the pre-helix loop consisting of residues Phe 49 to Asn 59, and on the receptor BRIA the short α-helix and flanking sequences (Asp 84 to Arg 97). Two hydrogen bonds, BMP-2 Asp 53 (N)-BRIA$_{EC}$ Cys 77 (O) and BMP-2 Ser 69 (O)-BRIA$_{EC}$ Gln 94 (N), are formed between main chain atoms only, two hydrogen bonds occur between side chains only and 4 mixed hydrogen bonds comprise side chain and main chain atoms (Table 1). Eight of these ten hydrogen bonds have donor-acceptor distances (2.8±0.14 Å) and φ bond angles (137±11°) as expected for bona fide hydrogen bonds (Xu et al., 1997). However, a classification of the strength of an individual hydrogen bond based purely on a geometrical evaluation of the bond parameters seems not possible for this complex.

In order to explore whether functionally important H-bonds can be predicted from the interface structure, the residual fractional accessibility was calculated (FIG. 1C). This residual accessibility in the complex correlates with the location of a residue towards the core or towards the periphery of the interface (Chakrabarti and Janin, 2002). Eight of the ten interfacial H-bonds occur between residues located at the periphery. Only the two H-bonds connecting receptor Gln 86 to the BMP-2 main chain of Leu 51 amide and carbonyl is completely buried upon complex formation (FIG. 1C). Consequently, this interaction might represent a hot spot of binding (Bogan and Thorn, 1998), whereas the other H-bonds and hydrophobic interactions might contribute not or only marginal to binding affinity.

Examination of water molecules in the interface reveals that the desolvation of the binding epitope is rather efficient compared to other protein-protein interfaces. Only four water molecules are completely buried in each ligand-receptor interface upon complex formation. The low temperature factors of these buried water molecules (i.e. values for these buried water molecules range from 40 to 50 Å$^2$ with protein atoms in close proximity having B-factors of 32 Å$^2$) suggest that exchange with external water might be slow. Surprisingly, these water molecules are in close proximity of the hot spot BRIA$_{EC}$ Gln 86. Three water molecules are located on the "membrane-distal side" of BRIA$_{EC}$ Gln 86 near to the side chain amide nitrogen atom. These hydrogen-bonded water molecules fill a larger cleft in the interface with BRIA$_{EC}$ Lys 97 blocking the entrance to this cavity. A single isolated water molecule is located in a hollow space next to the side chain carbonyl oxygen atom of BRIA$_{EC}$ Gln 86. This cavity is blocked from the outside by the residues Phe 49 and Pro 50 of BMP-2. The incomplete desolvation of receptor Gln 86 during BMP-2 binding possibly supports the formation of a strong hydrogen bond in a hydrophobic environment.

EXAMPLE 3

Mutational Analysis of Hydrogen Bonds

The importance of hydrogen bonds for binding affinity was analysed by interaction analysis employing BMP-2 and BRI-

TABLE 1

Geometry of H-bonds in the BMP-2 - BRIA interface.

| BRIA$_{EC}$ | BMP-2 | Distance Å | Angle NOC[b] | H-bond[c] | Mutein[d] |
|---|---|---|---|---|---|
| T55 (OG1) | D53 (OD2) | 2,73 (2,79) | 127 (127) | SC-SC | *D53A/D53P* |
| C77 (O) | D53 (N) | 2,88 (2,86) | 136 (131) | MC-MC | D53P |
| ▨▨▨ | ▨▨▨ | ▨▨▨ | ▨▨▨ | ▨▨▨ | ▨▨▨ |
| D84 (OD2) | Y103 (OH) | 2,79 (2,64) | 147 (155) | SC-SC | Y103A |
| Q86 (OE1) | L51 (N) | 2,75 (2,76) | 127 (127) | SC-MS | Q86A/*L51P* |
| Q86 (NE2) | L51 (O) | 2,97 (3,02) | 134 (133) | SC-MC | Q86A |
| D89 (O) | W28 (NE1) | 2,88 (2,87) | 135 (123) | MC-SC | W28F |
| S90 (OG) | V26 (O) | 2,53 (2,62) | 128 (134) | SC-MC | S90A |
| Q94 (N) | S69 (O) | 2,87 (2,88) | 151 (153) | MC-MC | Q94P |
| ▨▨▨ | ▨▨▨ | ▨▨▨ | ▨▨▨ | ▨▨▨ | ▨▨▨ |
| mean value[a] | | 2,8 (2,78) | 137 (137) | | |
| S.D. | | 0,14 (0,14) | 10 (13) | | |

The numbers in bracket represent the distances of donor-acceptor atom and angles in the second interface related by non-crystallographic symmetry.
[a] H-bonds in the shaded rows were excluded from above geometrical statistics;
[b] N—O—C are the Donor-Acceptor atoms, from statistics (Xu et al., 1997) this angle is 149° ± 15° for MC-MC hydrogen bonds and 129° ± 18° for SC-MC and SC-SC H-bonds;
[c] MC (main chain) and SC (sside chain) donor/acceptor atoms;
[d] Analysed H-bond disrupting ssubstitutions in BMP-2 (italic) and BRIA (bold).

$A_{EC}$ muteins with two kinds of amino acid substitutions. First, alanine substitutions were introduced to disrupt side chain bonds (see table 1 in example 2). Because the BMP-2 W28A mutein could not be isolated Trp 28 was substituted by phenylalanine whose side chain is also devoid of hydrogen bonding capacity. (One charged residue substitution was done in the BMP-2 S69R mutein.) Second, proline substitutions were introduced to abolish hydrogen bonding by the main chain amide group.

Interaction analysis of BMP-2 muteins with immobilised receptor $BRIA_{EC}$ as represented in table 2 showed that substitutions W28F, D53A and Y103A had only small effects on binding affinity. A slightly higher reduction in binding affinity (17 fold) was observed after charged residue insertion in the S69R mutein. Remarkably, the L51P and the D53P substitutions lead to dramatic lower affinities. The apparent dissociation constant $K_D$ between $BRIA_{EC}$ and L51P is more than 7100 times higher than that of BMP-2, and 53 times higher for D53P (Table 2 and FIG. 7. Both muteins have a similar drop in the affinity for the BRIB receptor indicating that the same determinants of BMP-2 are used for binding of the two type I receptors. This suggests that the main chain hydrogen bonds disrupted in the two proline muteins are major binding determinants, whereas the side chain bonds of W28, D53, S69 and Y103 are of minor importance for binding to the BRIA receptor.

The affinity of the proline muteins for the type II receptor ARII is unaltered in comparison to the wild type (Table 2). The same has been observed for interaction with type II receptors Activin receptor IIB and BMP receptor II (data not shown). This confirms that the gross structure of the mutein is unchanged, since the local structural alteration due to the substituted proline is not propagated to the juxtaposed epitope for type II receptor binding (knuckle epitope).

TABLE 2

Binding affinities between BMP-2 muteins and the receptor ectodomains BRIA, BRIB and ARII, as well as between BMP-2 wild type and $BRIA_{EC}$ muteins.

| | Immobilised receptor EC | | |
|---|---|---|---|
| Ligand | BRIA | BRIB | ARII |
| | $K_{D(Mut)}/K_{D(WT)}$ | | |
| BMP-2 | 1 (=0.91 nM) | 1 (=3.6 nM) | 1 (=14 nM) |
| BMP-2 W28F | 3.5 | 1.7 | 1.2 |
| BMP-2 L51P | >7100 | >920 | 2.3 |
| BMP-2 D53A | 0.91 | 0.34 | 1.2 |
| BMP-2 D53P | 53 | 10 | 1.2 |
| BMP-2 S69R | 17 | n.d. | 0.9 |
| BMP-2 Y103A | 7.8 | 3.2 | 1.4 |

| | Immobilised receptor EC | | |
|---|---|---|---|
| Ligand | BRIA Q86A | BRIA S90A | BRIA Q94P |
| | $K_{D(mut)}/K_{D(WT)}$ | | |
| BMP-2 | 86 | 2.6 | 3.1 |

Figure 2:
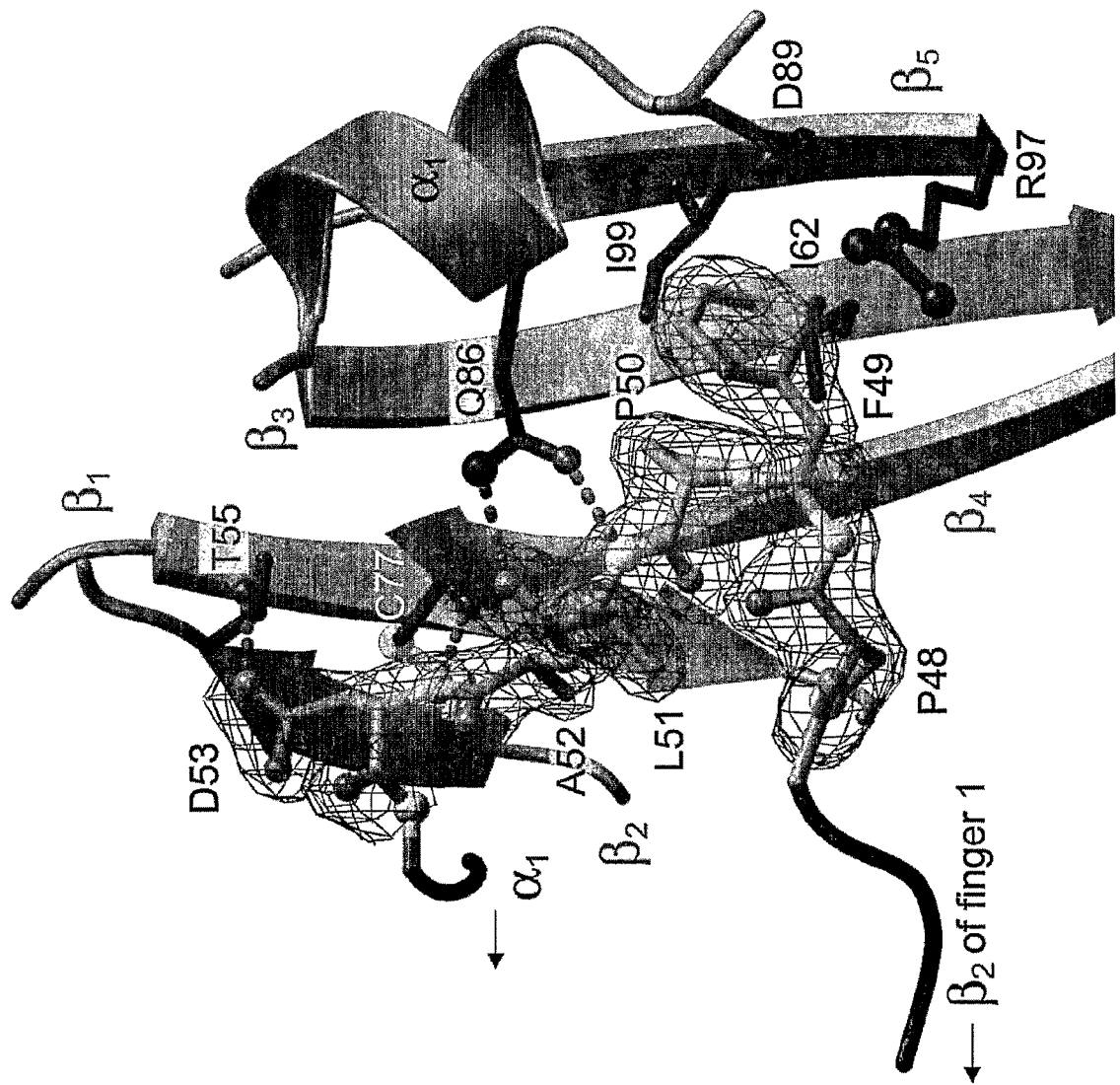
FIG. 2 shows a zoom-in into the interface of the BMP-2-BRIA interaction.

In order to identify binding determinants of the BRIA receptor three ectodomain muteins were prepared. In the receptor Q94P mutein the backbone nitrogen amide donating in the wild type a hydrogen bond to BMP-2 Ser 69 backbone carbonyl has been disrupted. The receptor Q86A mutein is devoid of the side chain carboxyamido group that in the wild type forms H-bond with BMP-2 L51 backbone amide and carbonyl (FIG. 2). The S90A substitution abolishes the serine hydroxyl group that donates a hydrogen bond to the BMP2 Val 26 backbone carbonyl. All receptor muteins could be highly purified after E. coli expression similar as the wild type ectodomain. When immobilised to the biosensor the receptor Q94P mutein bound BMP-2 with an only 3 times reduced affinity compared to the wild type ectodomain (Table 2) indicating that the main chain/main chain bond lost in the mutein contributes only marginally to binding. A similarly small change in affinity is observed in the S90A mutein.

The receptor Q86A substitution, however, resulted in an 86-fold increased $K_D$ during BMP-2 interaction. Such a large decrease in affinity was however expected, since the BMP-2 L51P mutein has already demonstrated that the affected H-bond represents a major binding determinant (see above). Most importantly, the hot spot identified by the mutational analysis coincides with the hot spot surmised by the analysis of the residual fractional accessibility of the engaged donor and acceptor groups (FIG. 1C). The loss in affinity in the receptor Q86A mutein is less severe than in the BMP-2 L51P mutein (Table 2). Neighbouring side chains in the receptor, e.g. Lys 79, or Glu 81, or Asp 89, might compensate partially for the carboxamide group of Gln 86 lost (FIG. 1b). On the other hand, the proline introduced in BMP-2 L51P causes steric hindrance or disturb nearby bonds by local structural rearrangements, e.g. between the BMP-2 Asp 53 backbone amide and the receptor Cys 77 carbonyl, and thereby would aggravate the effect of the substitution (FIG. 2).

EXAMPLE 4

Structure of Proline BMP-2 Mutein L51P

Comparing the large decrease in binding affinity of BMP-2 L51P with that observed for $BRIA_{EC}$ Q86A suggests that the loss in binding affinity might result not only from the loss of a single hydrogen bond. In addition larger structural changes in the binding epitope might disrupt the protein interaction. Therefore, BMP-2 L51P and also D53P muteins were submitted to crystallisation trials. BMP-2 L51P could be crystallised under the same conditions as wild type BMP-2, with identical crystal parameters, e.g. the same space group, R32, and almost identical cell constants as observed for crystals of wild type BMP-2. Apparently, the proline residue can be accommodated in place of Leu 51 whose hydrophobic side chain points into the protein core of BMP-2. The mutein D53P did not crystallise under those conditions, crystals of D53P growing from either ethanol or 2-methyl-2,4-pentandiol diffracted only to very low resolution and were not further analysed.

Diffraction data for BMP-2 L51P were obtained at room temperature to a resolution of 2.7 Å. Apart from the site of mutation the structures of BMP-2 wild type and L51P are basically identical within the error boundaries of the structure determination method depicted in table 3; the r.m.s. deviation for all $C_\alpha$ atom positions is 0.6 Å. Clear changes are observed in the pre-helix loop comprising residues Pro 48 to His 54 carrying also the site of mutation at position 51. For residues Pro 48, Phe 49, Pro 50, Leu/Pro51, Ala 52, and His 54 the distances between the $C_\alpha$-position of the wild type and mutein exceeds 1 Å, with the largest difference of 1.8 Å for the $C_\alpha$ of Ala 52 (table 3). Since the overall positional error for both structures, BMP-2 wild type and L51P, is about 0.4 as calculated from $\sigma_A$-plot, the change in conformation for the pre-helix loop might be considered small but significant.

TABLE 3

Processing and refinement statistics for BMP-2 - BRIA complex and BMP-2 L51P.

|  | BMP-2 - BRIA complex | BMP-2 L51P |
|---|---|---|
| *Crystals and data processing* | | |
| Beamline | X06SA SLS | home source |
| Wave length (Å) | 0.918 | 1.541 |
| Space group | P65 | R32 |
| Unit cell | a = b = 107.49 Å, | a = b = 94.29 Å, |
|  | c = 102.28 Å | c = 102.88 Å, |
|  | $\alpha = \beta = 90°, \gamma = 120°$ | $\alpha = \beta = 90°, \gamma = 120°$ |
| Resolution (Å) | 20.0-1.86 (1.91-1.86) | 20.0-2.65 (2.82-2.65) |
| Number of collected reflections | 247856 (21558) | 19336 (615) |
| Number of unique reflections | 54306 (7758) | 5624 (377) |
| Completeness | 96.8 (94.9) | 93.5 (72.3) |
| Multiplicity | 4.6 (2.8) | 3.4 (1.6) |
| Rsym (%) for all reflections | 8.3 (55.6) | 6.0 (29.3) |
| <Intensity/σ> | 4.4 (1.2) | 8.8 (2.4) |
| *Refinement statistics* | | |
| Rcryst (%) | 20.7 (36.6) | 21.5 (33.2) |
| Rfree (%) (test set 5%) | 22.9 (39.6) | 23.5 (33.6) |
| *r.m.s. deviation* | | |
| Bonds (Å) | 0.017 | 0.006 |
| Angles (deg.) | 1.537 | 1.226 |
| Dihedrals (deg.) | 27.334 | 24.733 |
| Impropers (deg.) | 1.388 | 0.910 |
| Average B-Factor (Å$^2$) | 36.1 | 64.6 |
| Coordinate error (cross-validated sigma) (Å) | 0.3 (0.3) | 0.4 (0.4) |
| *Procheck analysis* | | |
| Residues in most favored region (%) | 87.2 | 85.2 |
| Residues in additional allowed region (%) | 11.3 | 13.6 |
| Residues in generously allowed region (%) | 1.5 | 1.1 |
| Residues in disallowed region (%) | 0.0 | 0.0 |

Figure 3:
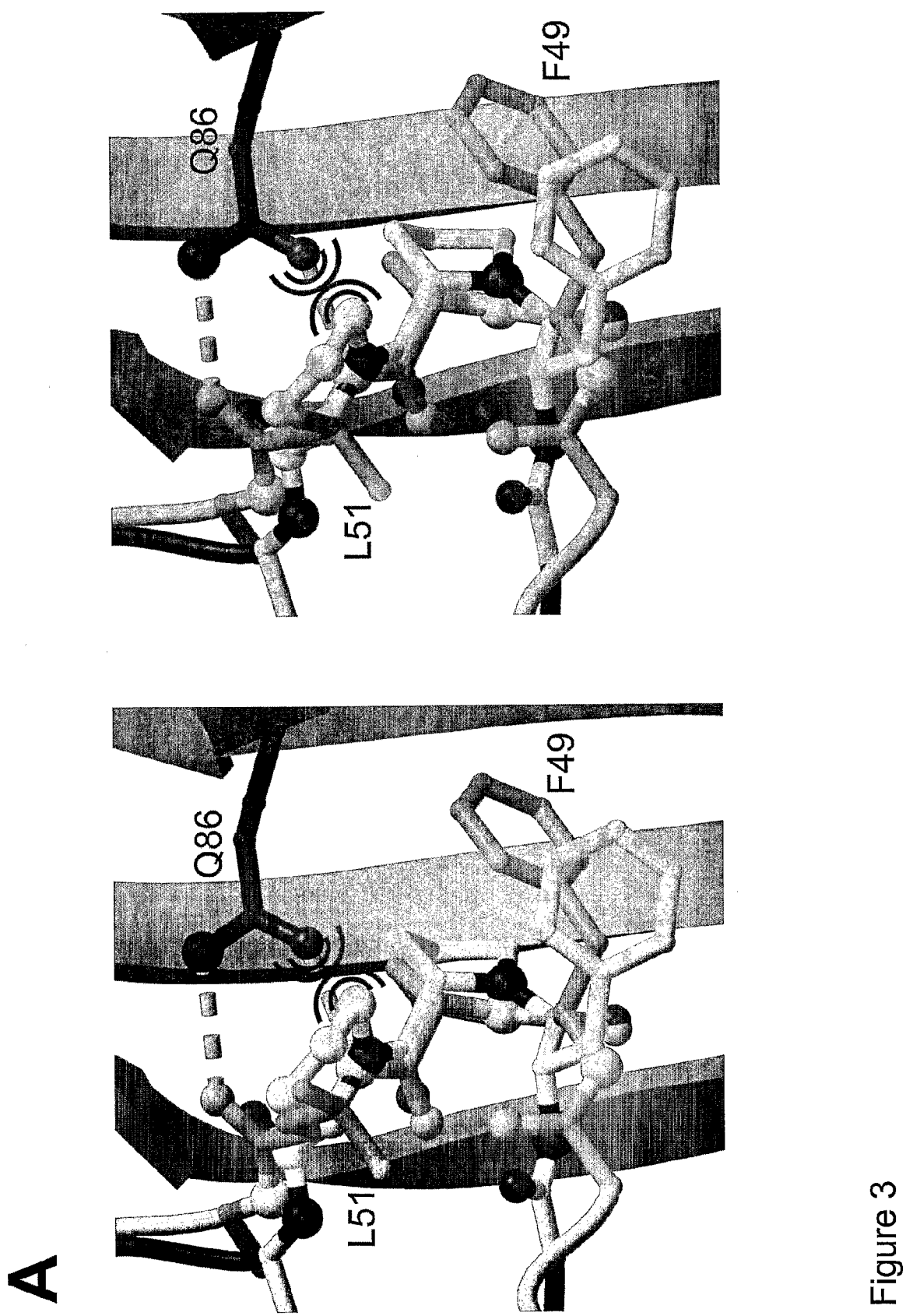
FIG. 3 (A) shows a stereo view of the pre-helix loop segment showing the crystal structure of the BMP-2 L51P.

This change may be due to altered backbone geometry for the proline residue compared to that for wild type leucine. However, comparing the structure of BMP-2 in its unbound and bound conformation, the differences between the $C_\alpha$ positions are of the same magnitude as observed between BMP-2 wild type and mutein L51P, showing that the conformation of the pre-helix loop is neither preformed nor fixated, and adapts on the receptor surface upon complex formation. The side chain of Pro 51 is oriented as Leu 51 in wild type BMP-2, indicating that the packing of the hydrophobic core is not affected by the mutation. Additionally, exchange of Leu 51 to proline does not alter the orientation of the backbone carbonyl of residue 51 therefore one hydrogen bond of residue 51 with BRIA Gln 86 might still be formed in the complex (FIGS. 2,3A). Considering the rather small structural differences introduced in the unbound proteins by the mutation the large change in binding affinity seems puzzling.

A superposition of the structure of L51P and the complex of BMP-2-BRIA$_{EC}$ reveals that the ring of the proline residue occupies the volume formerly used for the hydrogen bond between the BMP-2 Leu 51 amide and the side chain carbonyl of BRIA$_{EC}$ Gln 86 (FIG. 3A). The larger spatial requirement for the proline ring introduces a steric hindrance between the side chains of BMP-2 Pro 51 and BRIA$_{EC}$ Gln 86 (FIG. 3A). To accommodate Pro 51 its side chain needs to be pushed further back. Due to the rigid ring structure which basically fixes the amide nitrogen with respect to the ring orientation this corresponds to a rotation around the φ backbone torsion angle moving the backbone carbonyl of Pro 50 towards the side chain of BRIA$_{EC}$ Gln 86 if the ring structure is pushed back. Consequently, by removing one steric hindrance another one is introduced possibly explaining the large loss in binding energy by the mutation L51P.

EXAMPLE 5

Proline Muteins and Biological Activity

Figure 4:
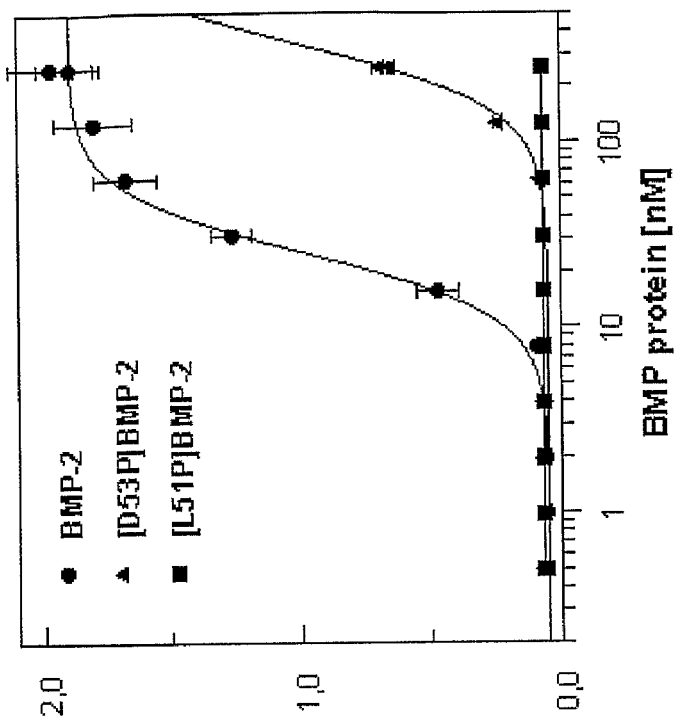
FIG. 4 shows the biological activity of BMP-2 proline muteins expressed as induction of alkaline phosphatase (ALP) activity measured in ATDC5 (A) and C2C12 (B) cells in response to BMP-2 and BMP-2 muteins.
Figure 4:
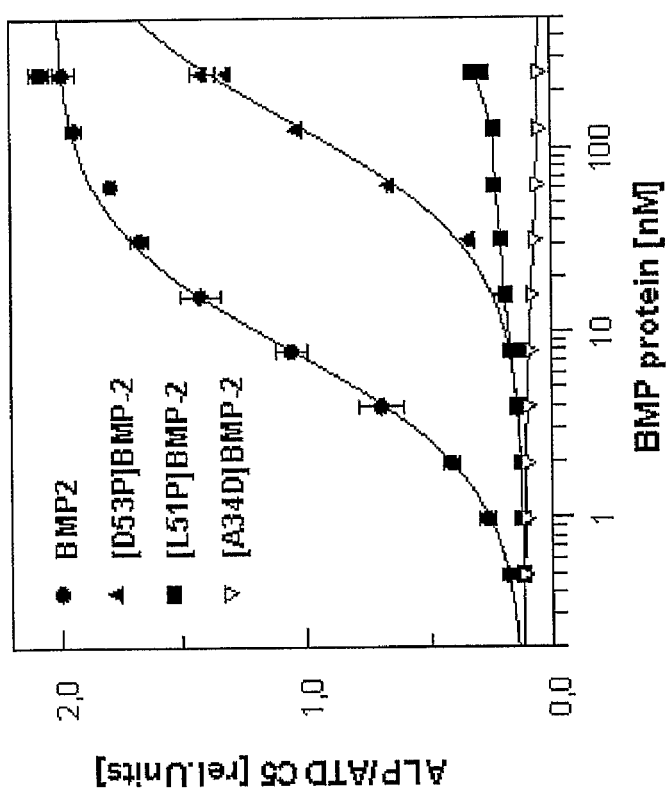

The biological activity of the BMP-2 proline muteins was determined by dose-dependent induction of alkaline phosphatase (ALP) activity using C2C12 cells as well as the slightly more sensitive ATDC5 cell line. The dose of wild type BMP-2 resulting in 50% of the maximal response (ED$_{50}$) was 25 nM in C2C12 cells. Using ATDC5 cells the ED$_{50}$ was 8 nM showing the increased responsiveness of these cells. In contrast, BMP-2 L51P has no measurable biological activity in C2C12 (>1600 nM) or in the ATDC5 cells (>1500 nM). The BMP-2 D53P mutein shows ED$_{50}$ values of 330 nM and 140 nM for C2C12 and ATDC5 cells, respectively. These values are about 13 to 17 times higher compared to the ED$_{50}$ value of wild type BMP-2. Thus, the different reduction of BRIA receptor affinity in the two BMP-2 proline muteins parallels the loss in biological activity (FIG. 4).

Since the proline substitution of BMP-2 Leu 51 is affecting only the interaction with the type I receptor while the affinity for the type II receptor is unaltered, the L51P mutein might principally function as a dominant-negative inhibitor. However, this was not observed when concentrations up to 250 μM of the mutein were applied to cells stimulated with 20 nM BMP-2 (data not shown). In comparison, the basal ALP activity in ATDC5 cells is inhibited by the antagonistic BMP-2 A34D mutein (Kirsch et al., 2000a), but not by L51P (FIG. 4A).

EXAMPLE 6

Proline Muteins as Antagonists of Binding Proteins

The lack of BMP-2 L51P to bind to BRIA$_{EC}$ raised the question, whether the interaction with other binding proteins might be also affected by the proline substitution. Of particular interest is Noggin that binds BMPs with high affinity and whose structure in complex with BMP-7 has been recently determined (Groppe et al., 2002). Another important binding protein is Chordin, that interacts with BMP-2 by means of two cysteine-rich domains. Still another type of binding protein represents Gremlin that interacts with BMP-2 via a so-called DAN domain. Each of the three proteins was immobilised at the surface of a biosensor and analysed for BMP-2 mutein interaction as depicted in table 4.

TABLE 4

Binding affinities between BMP-2 proline muteins and Noggin, Chordin, and Gremlin (Biacore interaction analysis).

| Ligand analyte | Immobilised binding protein | | | |
| --- | --- | --- | --- | --- |
| | Noggin | Chordin CR1 | Chordin CR3 | Gremlin |
| | $K_{D(mut)}/K_{D(WT)}$ | | | |
| BMP-2 | 1 (=1.9 nM) | 1 (=61 nM) | 1 (=67 nM) | 1 (=22 nM) |
| BMP-2 D53P | 1.3 | 0.7 | 1.1 | 0.7 |
| BMP-2 L51P | 0.27 | 0.85 | 0.9 | 0.55 |

The dissociation constants $K_D$ of the two BMP-2 proline muteins for the complex with Noggin were similar to those of BMP-2 wild type and ranged from 0.5 to 2.5 nM. Thus, BMP-2 Leu 51 and Asp 53 are not the main binding determinants for Noggin, despite the fact that the N-terminal amino acids of Noggin have been shown to be in contact with the BMP-7 region corresponding to BMP-2 Leu 51 (BMP-7 Leu 75) and Asp 53 (BMP-7 Ser 77, pre-helix loop) and that Noggin prevents BRIA binding to BMP-2.

The affinity of BMP-2 for Chordin domain CR1 and CR3 as well as for Gremlin is 10 to 30 times lower than that for Noggin (table 4). Again a similar dissociation constant $K_D$ is found for BMP-2 wild type or the two proline muteins, indicating that the binding of these proteins is not affected by the proline substitutions. Thus the BMP-2 epitopes for both binding proteins differ from that for the BRIA receptor.

EXAMPLE 7

Proline Mutein L51P Releases Noggin Inhibition in C2C12 Cells

Figure 5:
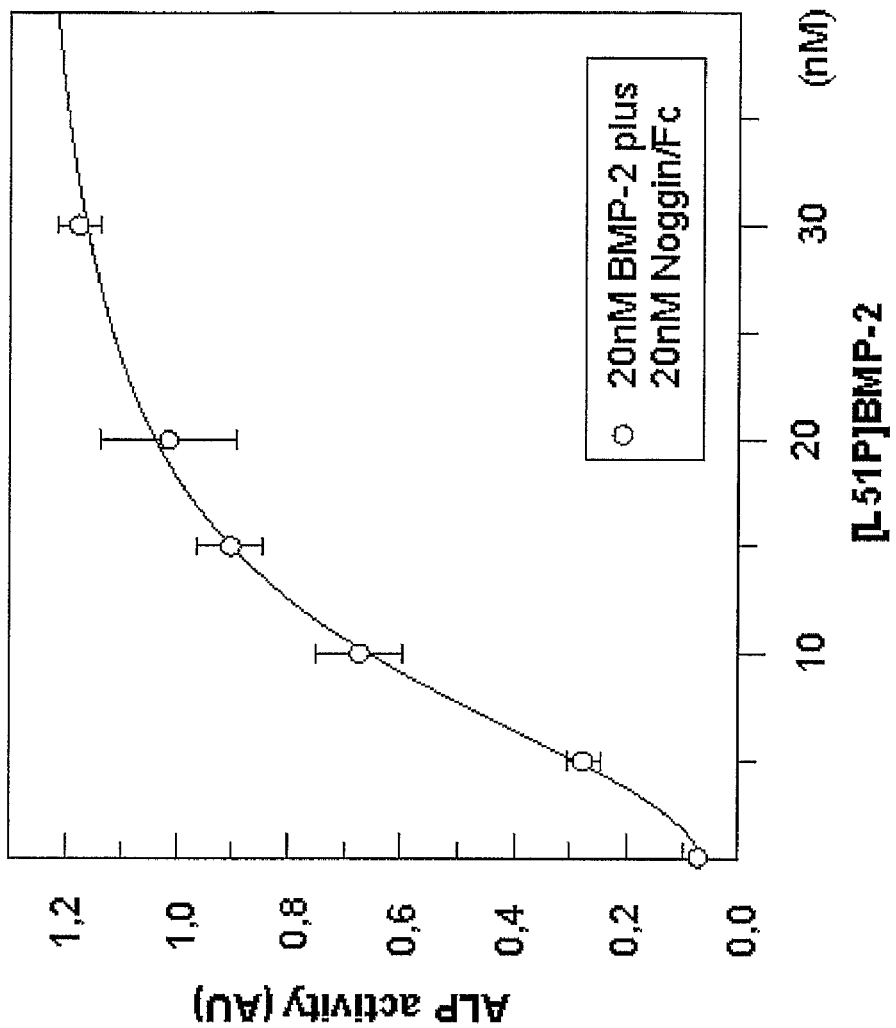
FIG. 5 shows the release of noggin inhibition by BMP-2 proline mutein L51P.
Figure 6:
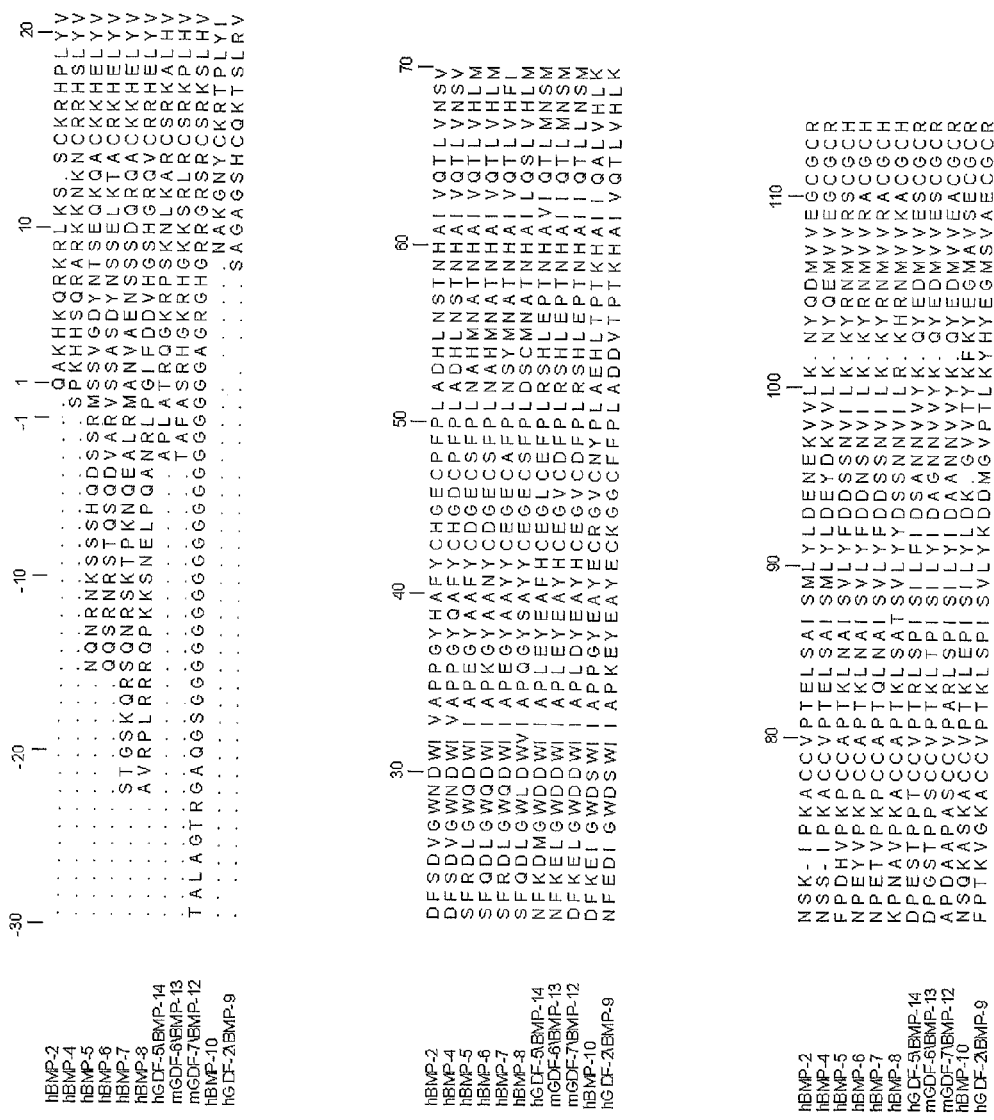
FIG. 6 shows an alignment of BMP-2 like proteins (SEQ ID NOs: 1, 3, 5, 7, 9, 11, 13, 15, 17, 19 and 21) which upon exchanging the amino acid residue at the position corresponding to amino acid position 51 of human BMP-2 from leucine to preferably proline form preferred embodiments of the muteins according to the present invention.

BMP-2 induces in starved promyeloblastic cell line C2C12 the expression of alkaline phosphatase. This BMP response is inhibited to background levels by equimolar concentration of Noggin-Fc fusion protein (FIG. 5). The inhibition of BMP-2 activity by Noggin is released in a dose dependent manner by the L51P mutein. At roughly equimolar concentrations of the mutein L51P and Noggin the inhibitory effect of Noggin is neutralized to more than 80%. This indicates that the receptor-dead L51P mutein represents an efficient inhibitor of the Noggin protein. This result is in accordance with the physical binding studies showing disruption of type I receptor binding and conservation of Noggin binding after the BMP-2 L51P substitution.

REFERENCES

In order to avoid unnecessary reference a comprehensive list of the references mentioned herein is presented in the following. It is to be understood that the disclosure of any of these references is incorporated herein by reference.

Balemans, W. and Van Hul, W. (2002) Extracellular regulation of BMP signaling in vertebrates: a cocktail of modulators. *Dev Biol*, 250, 231-250.

Bogan, A. A. and Thorn, K. S. (1998) Anatomy of hot spots in protein interfaces. *J Mol Biol*, 280, 1-9.

Boulanger, M. J., Chow, D. C., Brevnova, E. E. and Garcia, K. C. (2003) Hexameric structure and assembly of the interleukin-6/IL-6 alpha-receptor/gp130 complex. *Science*, 300, 2101-2104.

Brunger, A. T. (1992) Free R value: a novel statistical quantity for assessing the accuracy of crystal structures. *Nature*, 355, 472-475.

Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. and Warren, G. L. (1998) Crystallography & NMR system: A new software suite for macromolecular structure determination. *Acta Crystallogr D Biol Crystallogr*, 54 (Pt 5), 905-921.

Chakrabarti, P. and Janin, J. (2002) Dissecting protein-protein recognition sites. *Proteins*, 47, 334-343.

Collaborative Computational Project, N. (1994) The CCP4 Suite: Programs for Protein Crystallography. *Acta Crystallog sect D*, 50.

de Vos, A. M., Ultsch, M. and Kossiakoff, A. A. (1992) Human growth hormone and extracellular domain of its receptor: crystal structure of the complex. *Science*, 255, 306-312.

Evans, P. R. (1993) Data reduction. *Proceedings of CCP4 Study Weekend*, pp. 114-122.

Greenwald, J., Groppe, J., Gray, P., Wiater, E., Kwiatkowski, W., Vale, W. and Choe, S. (2003) The BMP7/ActRII extracellular domain complex provides new insights into the cooperative nature of receptor assembly. *Mol Cell*, 11, 605-617.

Groppe, J., Greenwald, J., Wiater, E., Rodriguez-Leon, J., Economides, A. N., Kwiatkowski, W., Affolter, M., Vale, W. W., Belmonte, J. C. and Choe, S. (2002) Structural basis of BMP signalling inhibition by the cystine knot protein Noggin. *Nature*, 420, 636-642.

Hage, T., Sebald, W. and Reinemer, P. (1999) Crystal structure of the interleukin-4/receptor alpha chain complex reveals a mosaic binding interface. *Cell*, 97, 271-281.

Hart, P. J., Deep, S., Taylor, A. B., Shu, Z., Hinck, C. S. and Hinck, A. P. (2002) Crystal structure of the human TbetaR2 ectodomain—TGF-beta3 complex. *Nat Struct Biol*, 9, 203-208.

Kirsch, T., Nickel, J. and Sebald, W. (2000a) BMP-2 antagonists emerge from alterations in the low-affinity binding epitope for receptor BMPR-II. *Embo J*, 19, 3314-3324.

Kirsch, T., Nickel, J. and Sebald, W. (2000b) Isolation of recombinant BMP receptor IA ectodomain and its 2:1 complex with BMP-2. *FEBS Lett*, 468, 215-219.

Leslie, A. G. W. (1992) Recent changes to the MOSFLM package for processing film and image plate data. *Joint CCP4+ESF-EAMCB Newsletter on Protein Crystallography*, 26.

McDonald, I. K. and Thornton, J. M. (1994) Satisfying hydrogen bonding potential in proteins. *J Mol Biol*, 238, 777-793.

Murshudov, G. N., Vagin, A. A. and Dodson, E. J. (1997) Refinement of Macromolecular Structures by the Maximum-Likelihood Method. *Acta Crystallog sect D*, D53, 240-255.

Ruppert, R., Hoffmann, E. and Sebald, W. (1996) Human bone morphogenetic protein 2 contains a heparin-binding site which modifies its biological activity. *Eur J Biochem*, 237, 295-302.

Syed, R. S., Reid, S. W., Li, C., Cheetham, J. C., Aoki, K. H., Liu, B., Zhan, H., Osslund, T. D., Chirino, A. J., Zhang, J., Finer-Moore, J., Elliott, S., Sitney, K., Katz, B. A., Matthews, D. J., Thompson, T. B., Woodruff, T. K. and Jardetzky, T. S. (2003) Structures of an ActRIIB:activin A complex reveal a novel binding mode for TGF-beta ligand: receptor interactions. *Embo J.* 22, 1555-1566.

Winn, M. D., Isupov, M. N. and Murshudov, G. N. (2001) Use of TLS parameters to model anisotropic displacements in macromolecular refinement. *Acta Crystallogr D Biol Crystallogr*, 57, 122-133.

Xu, D., Tsai, C. J. and Nussinov, R. (1997) Hydrogen bonds and salt bridges across protein-protein interfaces. *Protein Eng*, 10, 999-1012.

The features of the present invention disclosed in the specification, the claims and/or the drawings may both separately and in any combination thereof be material for realizing the invention in various forms thereof.

The invention claimed is:

1. A mutein of a bone morphogenetic protein, whereby the mutein consist of an amino acid substitution compared to the wild type of the bone morphogenetic protein, whereby the leucine in the wild type of the bone morphogenetic protein at the amino acid position corresponding to amino acid position 51 of human BMP-2 is proline in the mutein.

2. The mutein according to claim 1, whereby the bone morphogenetic protein is selected from the group consisting of hBMP-2, hBMP-4, hBMP-5, hBMP-6, hBMP-7, hBMP-8, hGDF-5, mGDF-6, mGDF-7, hBMP-10 and hGDF-2.

3. The mutein according to claim 2, whereby
the bone morphogenetic protein is hBMP-2 and the position corresponding to amino acid position 51 of human BMP-2 is amino acid position 51;
the bone morphogenetic protein is hBMP-4 and the position corresponding to amino acid position 51 of human BMP-2 is amino acid position 53;
the bone morphogenetic protein is hBMP-5 and the position corresponding to amino acid position 51 of human BMP-2 is amino acid position 68;
the bone morphogenetic protein is hBMP-6 and the position corresponding to amino acid position 51 of human BMP-2 is amino acid position 68;
the bone morphogenetic protein is hBMP-7 and the position corresponding to amino acid position 51 of human BMP-2 is amino acid position 75;
the bone morphogenetic protein is hBMP-8 and the position corresponding to amino acid position 51 of human BMP-2 is amino acid position 75;
the bone morphogenetic protein is hGDF-5 and the position corresponding to amino acid position 51 of human BMP-2 is amino acid position 56;
the bone morphogenetic protein is mGDF-6 and the position corresponding to amino acid position 51 of human BMP-2 is amino acid position 56;
the bone morphogenetic protein is mGDF-7 and the position corresponding to amino acid position 51 of human BMP-2 is amino acid position 82;
the bone morphogenetic protein is hBMP-10 and the position corresponding to amino acid position 51 of human BMP-2 is amino acid position 44; and
the bone morphogenetic protein is hGDF-2 and the position corresponding to amino acid position 51 of human BMP-2 is amino acid position 45.

4. The mutein according to claim 3, wherein the wild type of
hBMP-2 comprises the amino acid sequence according to SEQ ID NO: 1;
hBMP-4 comprises the amino acid sequence according to SEQ ID NO: 3;
hBMP-5 comprises the amino acid sequence according to SEQ ID NO: 5;
hBMP-6 comprises the amino acid sequence according to SEQ ID NO: 7;
hBMP-7 comprises the amino acid sequence according to SEQ ID NO: 9;
hBMP-8 comprises the amino acid sequence according to SEQ ID NO: 11;
hGDF-5 comprises the amino acid sequence according to SEQ ID NO: 13;
mGDF-6 comprises the amino acid sequence according to SEQ ID NO: 15;
mGDF-7 comprises the amino acid sequence according to SEQ ID NO: 17;
hBMP-10 comprises the amino acid sequence according to SEQ ID NO: 19; and
hGDF-2 comprises the amino acid sequence according to SEQ ID NO: 21.

5. The mutein according to claim 4, whereby the wild type of hBMP-2 is encoded by a nucleic acid according to SEQ ID NO: 2;
hBMP-4 is encoded by a nucleic acid according to SEQ ID NO: 4;
hBMP-5 is encoded by a nucleic acid according to SEQ ID NO: 6;
hBMP-6 is encoded by a nucleic acid according to SEQ ID NO: 8;
hBMP-7 is encoded by a nucleic acid according to SEQ ID NO: 10;
hBMP-8 is encoded by a nucleic acid according to SEQ ID NO: 12;
hGDF-5 is encoded by a nucleic acid according to SEQ ID NO: 14;
mGDF-6 is encoded by a nucleic acid according to SEQ ID NO: 16;
mGDF-7 is encoded by a nucleic acid according to SEQ ID NO: 18;
hBMP-10 is encoded by a nucleic acid according to SEQ ID NO: 20; and
hGDF-2 is encoded by a nucleic acid according to SEQ ID NO: 22.

6. The bone morphogenetic mutein according to claim 1, whereby the bone morphogenetic protein is BMP-2 or pro-BMP-2.

7. A nucleic acid coding for a bone morphogenetic mutein according to claim 1 and/or the complement thereof.

8. The nucleic acid according to claim 7, wherein the nucleic acid comprises the nucleic acid sequence according to SEQ ID NO: 2, 4, 6, 8, 10, 12, 14, 16, 18, 20 or 22, and/or the complement thereof.

9. A vector comprising a nucleic acid according to claim 7.

10. A cell comprising a nucleic acid according to claim 7.

11. A method for the production of a bone morphogenetic mutein, comprising the steps of
a) cultivating a cell according to claim 10 in a cultivation broth and b) preparing the bone morphogenetic mutein from the cell and/or from the cultivation broth.

12. A composition comprising a nucleic acid according to claim 7, and a pharmaceutically acceptable carrier.

13. A composition comprising a mutein according to claim 1 and a pharmaceutically acceptable carrier.

14. A method for inhibiting a BMP antagonist selected from the group consisting of the noggin protein family, the DAN protein family and the chordin protein family, comprising administering to a patient a bone morphogenetic mutein according to claim 1.

15. A bone morphogenetic protein comprising the amino acid sequence according to any of SEQ ID NOs: 23 to 33.

16. A method for the treatment of a disease selected from the group consisting of fibrotic diseases, wound healing, hypervascularization, vascular diseases, fractures, and osteoporosis comprising administering to a patient in need of such treatment a mutein of a bone morphogenetic protein, whereby the mutein consist of an amino acid substitution compared to the wild type of the bone morphogenetic protein, whereby the leucine in the wild type of the bone morphogenetic protein at the amino acid position corresponding to amino acid position 51 of human BMP-2 is substituted, whereby the mutein binds to a BMP antagonist selected from the group consisting of the noggin protein family, the DAN protein family and the chordin protein family, whereby the mutein does not bind to BMP receptor BRIA or BRIB.

17. The method according to claim 16, whereby the fibrotic disease is selected from the group consisting of renal fibrosis, hepatic cirrhosis, pulmonary fibrosis and chronic inflammation.

18. The method according to claim 16, wherein the wound healing is associated with keloid, cicatrization, or peritoneal obliteration.

19. The method according to claim 16, whereby the hypervascularization is associated with retinopathies, arteriosclerosis and/or tumors.

20. The method according to claim 16, whereby the fractures are non-healing fractures.

21. The method according to claim 16, whereby the disease is osteoporosis.

22. The method according to 16, whereby the leucine in the wild type of the bone morphogenetic protein at the amino acid position corresponding to amino acid position 51 of human BMP-2 is substituted to proline.

* * * * *

SEQUENCE LISTING

```
<160> NUMBER OF SEQ ID NOS: 33

<210> SEQ ID NO 1
<211> LENGTH: 114
<212> TYPE: PRT
<213> ORGANISM: Homo sapiens
<220> FEATURE:
<221> NAME/KEY: MISC_FEATURE
<222> LOCATION: (1)..(114)
<223> OTHER INFORMATION: BMP-2

<400> SEQUENCE: 1

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 2
<211> LENGTH: 345
<212> TYPE: DNA
<213> ORGANISM: Homo sapiens
<220> FEATURE:
<221> NAME/KEY: misc_feature
<222> LOCATION: (1)..(345)
<223> OTHER INFORMATION: BMP-2

<400> SEQUENCE: 2
caagccaaac acaaacagcg gaaacgcctt aagtccagct gtaagagaca ccctttgtac      60
gtggacttca gtgacgtggg gtggaatgac tggattgtgg ctccccggg gtatcacgcc     120 ttttactgcc acggagaatg ccctttttcct ggctgatc atctgaactc cactaatcat     180
gccattgttc agacgttggt caactctgtt aactctaaga ttcctaaggc atgctgtgtc     240
```

```
ccgacagaac tcagtgctat ctcgatgctg taccttgacg agaatgaaaa ggttgtatta      300
aagaactatc aggacatggt tgtggagggt tgtgggtgtc gctag                      345
```

<210> SEQ ID NO 3
<211> LENGTH: 116
<212> TYPE: PRT
<213> ORGANISM: Homo sapiens
<220> FEATURE:
<221> NAME/KEY: MISC_FEATURE
<222> LOCATION: (1)..(116)
<223> OTHER INFORMATION: BMP-4

<400> SEQUENCE: 3

```
Ser Pro Lys His His Ser Gln Arg Ala Arg Lys Lys Asn Lys Asn Cys
1               5                  10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115
```

<210> SEQ ID NO 4
<211> LENGTH: 351
<212> TYPE: DNA
<213> ORGANISM: Homo sapiens
<220> FEATURE:
<221> NAME/KEY: misc_feature
<222> LOCATION: (1)..(351)
<223> OTHER INFORMATION: BMP-4

<400> SEQUENCE: 4

```
agccctaagc atcactcaca gcgggccagg aagaagaata agaactgccg gcgccactcg      60
ctctatgtgg acttcagcga tgtgggctgg aatgactgga ttgtggcccc accaggctac     120
caggccttct actgccatgg ggactgcccc tttccactgg ctgaccacct caactcaacc     180
aaccatgcca ttgtgcagac cctggtcaat tctgtcaatt ccagtatccc caaagcctgt     240
tgtgtgccca ctgaactgag tgccatctcc atgctgtacc tggatgagta tgataaggtg     300
gtactgaaaa attatcagga gatggtagta gagggatgtg ggtgccgctg a              351
```

<210> SEQ ID NO 5
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: BMP-5

<400> SEQUENCE: 5

```
Asn Gln Asn Arg Asn Lys Ser Ser Ser His Gln Asp Ser Ser Arg Met
1               5                  10                  15
```

```
Ser Ser Val Gly Asp Tyr Asn Thr Ser Glu Gln Lys Gln Ala Cys Lys
            20                  25                  30

Lys His Glu Leu Tyr Val Ser Phe Arg Asp Leu Gly Trp Gln Asp Trp
        35                  40                  45

Ile Ile Ala Pro Glu Gly Tyr Ala Ala Phe Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Phe Pro Asp His Val Pro Lys Pro Cys
                85                  90                  95

Cys Ala Pro Thr Lys Leu Asn Ala Ile Ser Val Leu Tyr Phe Asp Asp
            100                 105                 110

Ser Ser Asn Val Ile Leu Lys Lys Tyr Arg Asn Met Val Val Arg Ser
            115                 120                 125

Cys Gly Cys His
        130

<210> SEQ ID NO 6
<211> LENGTH: 399
<212> TYPE: DNA
<213> ORGANISM: Homo sapiens
<220> FEATURE:
<221> NAME/KEY: misc_feature
<222> LOCATION: (1)..(399)
<223> OTHER INFORMATION: BMP-5

<400> SEQUENCE: 6 aatcaaaaacc gcaataaatc cagctctcat caggactcct ccagaatgtc cagtgttgga      60
gattataaca caagtgagca aaaacaagcc tgtaagaagc acgaactcta tgtgagcttc     120
cgggatctgg gatggcagga ctggattata gcaccagaag gatacgctgc attttattgt     180
gatggagaat gttctttttcc acttaacgcc catatgaatg ccaccaacca cgctatagtt     240
cagactctgg ttcatctgat gtttcctgac cacgtaccaa agccttgttg tgctccaacc     300
aaattaaatg ccatctctgt tctgtacttt gatgacagct ccaatgtcat tttgaaaaaa     360
tatagaaata tggtagtacg ctcatgtggc tgccactaa                            399

<210> SEQ ID NO 7
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: BMP-6

<400> SEQUENCE: 7

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
        35                  40                  45

Ile Ile Ala Pro Lys Gly Tyr Ala Ala Asn Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95
```

```
Cys Ala Pro Thr Lys Leu Asn Ala Ile Ser Val Leu Tyr Phe Asp Asp
            100                 105                 110

Asn Ser Asn Val Ile Leu Lys Lys Tyr Arg Asn Met Val Val Arg Ala
        115                 120                 125

Cys Gly Cys His
    130

<210> SEQ ID NO 8
<211> LENGTH: 399
<212> TYPE: DNA
<213> ORGANISM: Homo sapiens
<220> FEATURE:
<221> NAME/KEY: misc_feature
<222> LOCATION: (1)..(399)
<223> OTHER INFORMATION: BMP-6

<400> SEQUENCE: 8
caacagagtc gtaatcgctc tacccagtcc caggacgtgg cgcgggtctc cagtgcttca      60
gattacaaca gcagtgaatt gaaaacagcc tgcaggaagc atgagctgta tgtgagtttc     120
caagacctgg gatggcagga ctggatcatt gcacccaagg ctatgctgc  caattactgt     180 gatggagaat gctccttccc actcaacgca cacatgaatg caaccaacca cgcgattgtg     240
cagaccttgg ttcaccttat gaaccccgag tatgtcccca accgtgctg  tcgccaact      300 aagctaaatg ccatctcggt tctttacttt gatgacaact ccaatgtcat tctgaaaaaa    360
tacaggaata tggttgtaag agcttgtgga tgccactaa                            399

<210> SEQ ID NO 9
<211> LENGTH: 139
<212> TYPE: PRT
<213> ORGANISM: Homo sapiens
<220> FEATURE:
<221> NAME/KEY: MISC_FEATURE
<222> LOCATION: (1)..(139)
<223> OTHER INFORMATION: BMP-7

<400> SEQUENCE: 9

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 10
<211> LENGTH: 420
<212> TYPE: DNA
```

<213> ORGANISM: Homo sapiens
<220> FEATURE:
<221> NAME/KEY: misc_feature
<222> LOCATION: (1)..(420)
<223> OTHER INFORMATION: BMP-7

<400> SEQUENCE: 10

```
tccacgggga gcaaacagcg cagccagaac cgctccaaga cgcccaagaa ccaggaagcc    60
ctgcggatgg ccaacgtggc agagaacagc agcagcgacc agaggcaggc ctgtaagaag   120
cacgagctgt atgtcagctt ccgagacctg gctggcagg actggatcat cgcgcctgaa   180
ggctacgccg cctactactg tgaggggag tgtgccttcc ctctgaactc ctacatgaac   240
gccaccaacc acgccatcgt gcagacgctg gtccacttca tcaacccgga aacggtgccc   300
aagccctgct gtgcgcccac gcagctcaat gccatctccg tcctctactt cgatgacagc   360
tccaacgtca tcctgaagaa atacagaaac atggtggtcc gggcctgtgg ctgccactag   420
```

<210> SEQ ID NO 11
<211> LENGTH: 139
<212> TYPE: PRT
<213> ORGANISM: Homo sapiens
<220> FEATURE:
<221> NAME/KEY: MISC_FEATURE
<222> LOCATION: (1)..(139)
<223> OTHER INFORMATION: BMP-8

<400> SEQUENCE: 11

```
Ala Val Arg Pro Leu Arg Arg Arg Gln Pro Lys Lys Ser Asn Glu Leu
1               5                  10                  15
Pro Gln Ala Asn Arg Leu Pro Gly Ile Phe Asp Asp Val His Gly Ser
            20                  25                  30
His Gly Arg Gln Val Cys Arg Arg His Glu Leu Tyr Val Ser Phe Gln
        35                  40                  45
Asp Leu Gly Trp Leu Asp Trp Val Ile Ala Pro Gln Gly Tyr Ser Ala
    50                  55                  60
Tyr Tyr Cys Glu Gly Glu Cys Ser Phe Pro Leu Asp Ser Cys Met Asn
65                  70                  75                  80
Ala Thr Asn His Ala Ile Leu Gln Ser Leu Val His Leu Met Lys Pro
                85                  90                  95
Asn Ala Val Pro Lys Ala Cys Cys Ala Pro Thr Lys Leu Ser Ala Thr
            100                 105                 110
Ser Val Leu Tyr Tyr Asp Ser Ser Asn Asn Val Ile Leu Arg Lys His
        115                 120                 125
Arg Asn Met Val Val Lys Ala Cys Gly Cys His
    130                 135
```

<210> SEQ ID NO 12
<211> LENGTH: 420
<212> TYPE: DNA
<213> ORGANISM: Homo sapiens
<220> FEATURE:
<221> NAME/KEY: misc_feature
<222> LOCATION: (1)..(420)
<223> OTHER INFORMATION: BMP-8

<400> SEQUENCE: 12

```
gcagtgaggc cactgaggag gaggcagccg aagaaaagca cgagctgcc gcaggccaac    60
cgactcccag ggatctttga tgacgtccac ggctcccacg gccggcaggt ctgccgtcgg   120
cacgagctct acgtcagctt ccaggacctc ggctggctgg actgggtcat cgctccccaa   180
```

```
ggctactcgg cctattactg tgaggggag tgctccttcc cactggactc ctgcatgaat       240
gccaccaacc acgccatcct gcagtccctg gtgcacctga tgaagccaaa cgcagtcccc       300
aaggcgtgct gtgcacccac caagctgagc gccacctctg tgctctacta tgacagcagc       360
aacaacgtca tcctgcgcaa gcaccgcaac atggtggtca aggcctgcgg ctgccactga       420

<210> SEQ ID NO 13
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: GDF-5

<400> SEQUENCE: 13

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 14
<211> LENGTH: 363
<212> TYPE: DNA
<213> ORGANISM: Homo sapiens
<220> FEATURE:
<221> NAME/KEY: misc_feature
<222> LOCATION: (1)..(363)
<223> OTHER INFORMATION: GDF-5

<400> SEQUENCE: 14
gccccactgg ccactcgcca gggcaagcga cccagcaaga accttaaggc tcgctgcagt        60
cggaaggcac tgcatgtcaa cttcaaggac atgggctggg acgactggat catcgcaccc       120
cttgagtacg aggctttcca ctgcgagggg ctgtgcgagt tcccattgcg ctcccacctg       180
gagcccacga atcatgcagt catccagacc ctgatgaact ccatggaccc cgagtccaca       240
ccacccacct gctgtgtgcc cacgcggctg agtcccatca gcatcctctt cattgactct       300
gccaacaacg tggtgtataa gcagtatgag gacatggtcg tggagtcgtg tggctgcagg       360
tag                                                                    363

<210> SEQ ID NO 15
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: GDF-6
```

<400> SEQUENCE: 15

```
Thr Ala Phe Ala Ser Arg His Gly Lys Arg His Gly Lys Lys Ser Arg
1               5                   10                  15
Leu Arg Cys Ser Arg Lys Pro Leu His Val Asn Phe Lys Glu Leu Gly
                20                  25                  30
Trp Asp Asp Trp Ile Ile Ala Pro Leu Glu Tyr Glu Ala Tyr His Cys
            35                  40                  45
Glu Gly Val Cys Asp Phe Pro Leu Arg Ser His Leu Glu Pro Thr Asn
        50                  55                  60
His Ala Ile Ile Gln Thr Leu Met Asn Ser Met Asp Pro Gly Ser Thr
65                  70                  75                  80
Pro Pro Ser Cys Cys Val Pro Thr Lys Leu Thr Pro Ile Ser Ile Leu
                85                  90                  95
Tyr Ile Asp Ala Gly Asn Asn Val Val Tyr Lys Gln Tyr Glu Asp Met
            100                 105                 110
Val Val Glu Ser Cys Gly Cys Arg
        115                 120
```

<210> SEQ ID NO 16
<211> LENGTH: 360
<212> TYPE: DNA
<213> ORGANISM: Mus musculus
<220> FEATURE:
<221> NAME/KEY: misc_feature
<222> LOCATION: (1)..(360)
<223> OTHER INFORMATION: GDF-6

<400> SEQUENCE: 16

```
accgccttcg ccagccgtca cggcaagcga catggcaaga agtccaggct gcgctgcagc      60
agaaagcctc tgcacgtgaa ttttaaggag ttaggctggg acgactggat tatcgcgccc     120
ctagagtacg aggcctatca ctgcgagggc gtgtgcgact tccgctgcg ctcgcacctt      180
gagcccacta accatgccat cattcagacg ctgatgaact ccatggaccc gggctccacc     240
ccgcctagct gctgcgttcc caccaaactg actcccatta gcatcctgta catcgacgcg     300
ggcaataatg tagtctacaa gcagtatgag gacatggtgg tggagtcctg cggctgtagg     360
```

<210> SEQ ID NO 17
<211> LENGTH: 146
<212> TYPE: PRT
<213> ORGANISM: Mus musculus
<220> FEATURE:
<221> NAME/KEY: MISC_FEATURE
<222> LOCATION: (1)..(146)
<223> OTHER INFORMATION: GDF-7

<400> SEQUENCE: 17

```
Thr Ala Leu Ala Gly Thr Arg Gly Ala Gln Gly Ser Gly Gly Gly Gly
1               5                   10                  15
Gly Gly Gly Gly Gly Gly Gly Gly Gly Gly Gly Gly Gly Gly Gly Gly
                20                  25                  30
Ala Gly Arg Gly His Gly Arg Arg Gly Arg Ser Arg Cys Ser Arg Lys
            35                  40                  45
Ser Leu His Val Asp Phe Lys Glu Leu Gly Trp Asp Asp Trp Ile Ile
        50                  55                  60
Ala Pro Leu Asp Tyr Glu Ala Tyr His Cys Glu Gly Val Cys Asp Phe
65                  70                  75                  80
Pro Leu Arg Ser His Leu Glu Pro Thr Asn His Ala Ile Ile Gln Thr
```

```
                    85                  90                  95
Leu Leu Asn Ser Met Ala Pro Asp Ala Ala Pro Ala Ser Cys Cys Val
            100                 105                 110

Pro Ala Arg Leu Ser Pro Ile Ser Ile Leu Tyr Ile Asp Ala Ala Asn
        115                 120                 125

Asn Val Val Tyr Lys Gln Tyr Glu Asp Met Val Val Glu Ala Cys Gly
    130                 135                 140

Cys Arg
145

<210> SEQ ID NO 18
<211> LENGTH: 438
<212> TYPE: DNA
<213> ORGANISM: Mus musculus
<220> FEATURE:
<221> NAME/KEY: misc_feature
<222> LOCATION: (1)..(438)
<223> OTHER INFORMATION: GDF-7

<400> SEQUENCE: 18
actgcgctgg ctgggactcg gggagcgcag ggaagcggtg gtggcggcgg tggcggtggc      60
ggcggcggcg gcggcggcgg cggcggcggc ggcggcgcag gcaggggcca cgggcgcaga     120
ggccggagcc gctgcagtcg caagtcactg cacgtggact ttaaggagct gggctgggac     180
gactggatca tcgcgccatt agactacgag gcataccact gcgagggcgt ttgcgacttt     240
cctctgcgct cgcacctgga gcctaccaac cacgccatca ttcagacgct gctcaactcc     300
atggcgcccg acgctgcgcc agcctcctgc tgcgtgcccg caaggctcag tcccatcagc     360
attctctaca tcgatgccgc caacaacgtg gtctacaagc agtacgaaga catggtggtg     420
gaggcctgcg gctgcagg                                                   438

<210> SEQ ID NO 19
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: BMP-10

<400> SEQUENCE: 19

Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30

Ala Tyr Glu Cys Arg Gly Val Cys Asn Tyr Pro Leu Ala Glu His Leu
        35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105

<210> SEQ ID NO 20
<211> LENGTH: 327
<212> TYPE: DNA
```

<213> ORGANISM: Homo sapiens
<220> FEATURE:
<221> NAME/KEY: misc_feature
<222> LOCATION: (1)..(327)
<223> OTHER INFORMATION: BMP-10

<400> SEQUENCE: 20

```
aacgccaaag gaaactactg taagaggacc ccgctctaca tcgacttcaa ggagattggg    60
tgggactcct ggatcatcgc tccgcctgga tacgaagcct atgaatgccg tggtgtttgt   120 aactacccccc tggcagagca tctcacaccc acaaagcatg caattatcca ggccttggtc   180
cacctcaaga attcccagaa agcttccaaa gcctgctgtg tgcccacaaa gctagagccc   240
atctccatcc tctatttaga caaaggcgtc gtcacctaca agtttaaaata cgaaggcatg   300 gccgtctccg aatgtggctg tagatag                                      327
```

<210> SEQ ID NO 21
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: GDF-2

<400> SEQUENCE: 21

```
Ser Ala Gly Ala Gly Ser His Cys Gln Lys Thr Ser Leu Arg Val Asn
  1               5                  10                  15

Phe Glu Asp Ile Gly Trp Asp Ser Trp Ile Ile Ala Pro Lys Glu Tyr
             20                  25                  30

Glu Ala Tyr Glu Cys Lys Gly Gly Cys Phe Phe Pro Leu Ala Asp Asp
         35                  40                  45

Val Thr Pro Thr Lys His Ala Ile Val Gln Thr Leu Val His Leu Lys
     50                  55                  60

Phe Pro Thr Lys Val Gly Lys Ala Cys Cys Val Pro Thr Lys Leu Ser
 65                  70                  75                  80

Pro Ile Ser Val Leu Tyr Lys Asp Asp Met Gly Val Pro Thr Leu Lys
                 85                  90                  95

Tyr His Tyr Glu Gly Met Ser Val Ala Glu Cys Gly Cys Arg
            100                 105                 110
```

<210> SEQ ID NO 22
<211> LENGTH: 333
<212> TYPE: DNA
<213> ORGANISM: Homo sapiens
<220> FEATURE:
<221> NAME/KEY: misc_feature
<222> LOCATION: (1)..(333)
<223> OTHER INFORMATION: GDF-2

<400> SEQUENCE: 22

```
agcgccgggg ctggcagcca ctgtcaaaag acctccctgc gggtaaactt cgaggacatc    60
ggctgggaca gctggatcat tgcacccaag gagtatgaag cctacgagtg taagggcggc   120
tgcttcttcc ccttggctga cgatgtgacg ccgacgaaac acgctatcgt gcagaccctg   180
gtgcatctca gttccccac aaaggtgggc aaggcctgct gtgtgcccac caaactgagc   240
cccatctccg tcctctacaa ggatgacatg ggggtgccca ccctcaagta ccattacgag   300
ggcatgagcg tggcagagtg tgggtgcagg tag                                333
```

<210> SEQ ID NO 23

```
<211> LENGTH: 114
<212> TYPE: PRT
<213> ORGANISM: Homo sapiens
<220> FEATURE:
<221> NAME/KEY: MISC_FEATURE
<222> LOCATION: (1)..(114)
<223> OTHER INFORMATION: BMP-2 mutein

<400> SEQUENCE: 23

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Pro Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 24
<211> LENGTH: 116
<212> TYPE: PRT
<213> ORGANISM: Homo sapiens
<220> FEATURE:
<221> NAME/KEY: MISC_FEATURE
<222> LOCATION: (1)..(116)
<223> OTHER INFORMATION: BMP-4 mutein

<400> SEQUENCE: 24

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Pro Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
            115

<210> SEQ ID NO 25
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: BMP-5 mutein
```

<400> SEQUENCE: 25

Asn Gln Asn Arg Asn Lys Ser Ser His Gln Asp Ser Ser Arg Met
1               5                   10                  15

Ser Ser Val Gly Asp Tyr Asn Thr Ser Glu Gln Lys Gln Ala Cys Lys
            20                  25                  30

Lys His Glu Leu Tyr Val Ser Phe Arg Asp Leu Gly Trp Gln Asp Trp
                35                  40                  45

Ile Ile Ala Pro Glu Gly Tyr Ala Ala Phe Tyr Cys Asp Gly Glu Cys
        50                  55                  60

Ser Phe Pro Pro Asn Ala His Met Asn Ala Thr Asn His Ala Ile Val
65                  70                  75                  80

Gln Thr Leu Val His Leu Met Phe Pro Asp His Val Pro Lys Pro Cys
                85                  90                  95

Cys Ala Pro Thr Lys Leu Asn Ala Ile Ser Val Leu Tyr Phe Asp Asp
            100                 105                 110

Ser Ser Asn Val Ile Leu Lys Lys Tyr Arg Asn Met Val Val Arg Ser
                115                 120                 125

Cys Gly Cys His
        130

<210> SEQ ID NO 26
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: BMP-6 mutein

<400> SEQUENCE: 26

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
                35                  40                  45

Ile Ile Ala Pro Lys Gly Tyr Ala Ala Asn Tyr Cys Asp Gly Glu Cys
        50                  55                  60

Ser Phe Pro Pro Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
            100                 105                 110

Asn Ser Asn Val Ile Leu Lys Lys Tyr Arg Asn Met Val Val Arg Ala
                115                 120                 125

Cys Gly Cys His
        130

<210> SEQ ID NO 27
<211> LENGTH: 139
<212> TYPE: PRT
<213> ORGANISM: Homo sapiens
<220> FEATURE:
<221> NAME/KEY: MISC_FEATURE
<222> LOCATION: (1)..(139)
<223> OTHER INFORMATION: BMP-7 mutein

<400> SEQUENCE: 27

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Pro Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 28
<211> LENGTH: 139
<212> TYPE: PRT
<213> ORGANISM: Homo sapiens
<220> FEATURE:
<221> NAME/KEY: MISC_FEATURE
<222> LOCATION: (1)..(139)
<223> OTHER INFORMATION: BMP-8 mutein

<400> SEQUENCE: 28

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Pro Asp Ser Cys Met Asn
65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

<210> SEQ ID NO 29
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: GDF-5 mutein

<400> SEQUENCE: 29

-continued

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Pro Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 30
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: GDF-6 mutein

<400> SEQUENCE: 30

Thr Ala Phe Ala Ser Arg His Gly Lys Arg His Gly Lys Lys Ser Arg
1               5                   10                  15

Leu Arg Cys Ser Arg Lys Pro Leu His Val Asn Phe Lys Glu Leu Gly
            20                  25                  30

Trp Asp Asp Trp Ile Ile Ala Pro Leu Glu Tyr Glu Ala Tyr His Cys
        35                  40                  45

Glu Gly Val Cys Asp Phe Pro Pro Arg Ser His Leu Glu Pro Thr Asn
    50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Tyr Lys Gln Tyr Glu Asp Met
            100                 105                 110

Val Val Glu Ser Cys Gly Cys Arg
        115                 120

<210> SEQ ID NO 31
<211> LENGTH: 146
<212> TYPE: PRT
<213> ORGANISM: Mus musculus
<220> FEATURE:
<221> NAME/KEY: MISC_FEATURE
<222> LOCATION: (1)..(146)
<223> OTHER INFORMATION: GDF-7 mutein

<400> SEQUENCE: 31

Thr Ala Leu Ala Gly Thr Arg Gly Ala Gln Gly Ser Gly Gly Gly Gly
1               5                   10                  15

Gly Gly Gly Gly Gly Gly Gly Gly Gly Gly Gly Gly Gly Gly
            20                  25                  30

Ala Gly Arg Gly His Gly Arg Arg Gly Arg Ser Arg Cys Ser Arg Lys

```
                35                  40                  45
Ser Leu His Val Asp Phe Lys Glu Leu Gly Trp Asp Asp Trp Ile Ile
 50                  55                  60

Ala Pro Leu Asp Tyr Glu Ala Tyr His Cys Glu Gly Val Cys Asp Phe
 65                  70                  75                  80

Pro Pro Arg Ser His Leu Glu Pro Thr Asn His Ala Ile Ile Gln Thr
                 85                  90                  95

Leu Leu Asn Ser Met Ala Pro Asp Ala Ala Pro Ala Ser Cys Cys Val
            100                 105                 110

Pro Ala Arg Leu Ser Pro Ile Ser Ile Leu Tyr Ile Asp Ala Ala Asn
        115                 120                 125

Asn Val Val Tyr Lys Gln Tyr Glu Asp Met Val Val Glu Ala Cys Gly
    130                 135                 140

Cys Arg
145

<210> SEQ ID NO 32
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: BMP-10 mutein

<400> SEQUENCE: 32

Asn Ala Lys Gly Asn Tyr Cys Lys Arg Thr Pro Leu Tyr Ile Asp Phe
 1               5                  10                  15

Lys Glu Ile Gly Trp Asp Ser Trp Ile Ile Ala Pro Pro Gly Tyr Glu
             20                  25                  30

Ala Tyr Glu Cys Arg Gly Val Cys Asn Tyr Pro Pro Ala Glu His Leu
         35                  40                  45

Thr Pro Thr Lys His Ala Ile Ile Gln Ala Leu Val His Leu Lys Asn
     50                  55                  60

Ser Gln Lys Ala Ser Lys Ala Cys Cys Val Pro Thr Lys Leu Glu Pro
 65                  70                  75                  80

Ile Ser Ile Leu Tyr Leu Asp Lys Gly Val Val Thr Tyr Lys Phe Lys
             85                  90                  95

Tyr Glu Gly Met Ala Val Ser Glu Cys Gly Cys Arg
            100                 105

<210> SEQ ID NO 33
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: GDF-2 mutein

<400> SEQUENCE: 33

Ser Ala Gly Ala Gly Ser His Cys Gln Lys Thr Ser Leu Arg Val Asn
 1               5                  10                  15

Phe Glu Asp Ile Gly Trp Asp Ser Trp Ile Ile Ala Pro Lys Glu Tyr
             20                  25                  30

Glu Ala Tyr Glu Cys Lys Gly Gly Cys Phe Phe Pro Pro Ala Asp Asp
         35                  40                  45

Val Thr Pro Thr Lys His Ala Ile Val Gln Thr Leu Val His Leu Lys
     50                  55                  60
```

```
-continued

Phe Pro Thr Lys Val Gly Lys Ala Cys Cys Val Pro Thr Lys Leu Ser
 65              70                  75                  80

Pro Ile Ser Val Leu Tyr Lys Asp Asp Met Gly Val Pro Thr Leu Lys
                 85                  90                  95

Tyr His Tyr Glu Gly Met Ser Val Ala Glu Cys Gly Cys Arg
                100                 105                 110
```